United States Patent
Yamamoto et al.

(10) Patent No.: US 11,052,091 B2
(45) Date of Patent: Jul. 6, 2021

(54) BRK INHIBITORY COMPOUND

(71) Applicant: ONO PHARMACEUTICAL CO., LTD., Osaka (JP)

(72) Inventors: Shingo Yamamoto, Osaka (JP); Masakuni Kurono, Osaka (JP); Atsushi Yoshida, Osaka (JP); Shingo Hotta, Osaka (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/472,192

(22) PCT Filed: Dec. 20, 2017

(86) PCT No.: PCT/JP2017/045786
§ 371 (c)(1),
(2) Date: Jun. 20, 2019

(87) PCT Pub. No.: WO2018/117177
PCT Pub. Date: Jun. 28, 2018

(65) Prior Publication Data
US 2020/0000810 A1    Jan. 2, 2020

(30) Foreign Application Priority Data
Dec. 21, 2016 (JP) .............. JP2016-247440

(51) Int. Cl.
| C07D 473/14 | (2006.01) |
| A61K 31/52 | (2006.01) |
| A61P 35/00 | (2006.01) |
| A61K 31/5377 | (2006.01) |
| A61K 31/538 | (2006.01) |
| C07D 473/16 | (2006.01) |

(52) U.S. Cl.
CPC ............ A61K 31/52 (2013.01); A61K 31/538 (2013.01); A61K 31/5377 (2013.01); A61P 35/00 (2018.01); C07D 473/16 (2013.01)

(58) Field of Classification Search
CPC ...... C07D 473/14; A61K 31/522; A61P 35/00
USPC ...................... 544/265; 514/263.2
See application file for complete search history.

(56) References Cited

FOREIGN PATENT DOCUMENTS

| WO | WO-2007/015877 A2 | 2/2007 |
| WO | WO-2007/140222 A2 | 12/2007 |
| WO | WO-2007/142755 A2 | 12/2007 |
| WO | WO-2009/024824 A1 | 2/2009 |
| WO | WO-2009/131687 A2 | 10/2009 |
| WO | WO-2016/208595 A | 12/2016 |

OTHER PUBLICATIONS

Hussain et al. World J Clin Oncol Aug. 10, 2014; 5(3): 299-310.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p. 4.*
Dermeret al., Bio/Technology, 1994, 12:320.*
Golub et al., Science, 286, 531-537, 1999.Golub et al., Science, 286, 531-537, 1999.*
Cohen et al., Current Opinion in Chemical Biology, 3,459-465, 1999.*
International Search Report for PCT/JP2017/045786 dated Mar. 20, 2018.
Hongbo Zeng et al. "Discovery of novel imidazo[1,2-a]pyrazin-8-amines as Brk/PTK6 inhibitors"; Bioorganic & Medicinal Chemistry Letters; Aug. 3, 2011; pp. 5870-5875.

* cited by examiner

*Primary Examiner* — Jeffrey H Murray
(74) *Attorney, Agent, or Firm* — Foley & Lardner LLP

(57) ABSTRACT

The present invention relates to a Brk inhibitory compound represented by general formula (I) (wherein, all symbols represent the same meanings as the symbols set forth in the specification), a salt thereof, an N-oxide thereof, a solvate thereof, or a prodrug of any of these.

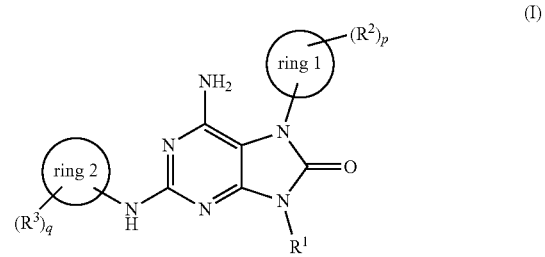

12 Claims, No Drawings

BRK INHIBITORY COMPOUND

CROSS-REFERENCE TO RELATED APPLICATIONS

The present application is a U.S. national stage application claiming the benefit of International Patent Application No. PCT/JP2017/045786, filed Dec. 20, 2017, which claims the benefit of priority to Japanese Patent Application No. 2016-247440, filed Dec. 21, 2016, the disclosures of which are hereby incorporated by reference.

TECHNICAL FIELD

The present invention relates to a Brk inhibitory compound, a salt thereof an N-oxide thereof, a solvate thereof, or a prodrug of any of these, and a medicament comprising the same as an active ingredient. Specifically, the present invention relates to a Brk inhibitory compound represented by the following general formula (I):

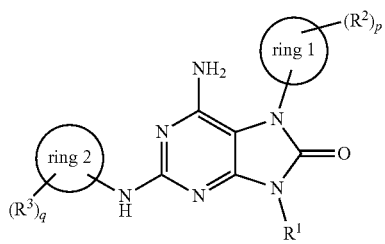

(I)

(wherein, all the symbols have the same meanings as described below), a salt thereof, an N-oxide thereof, a solvate thereof, or a prodrug of any of these (hereinafter, referred to as the compound of the present invention), and a medicament comprising the same as an active ingredient.

BACKGROUND ART

Brk (Breast tumor kinase) is also referred to as PTK6 (protein tyrosine kinase 6), and is a non-receptor tyrosine kinase which belongs to FRK (Fyn-related kinase)/PTK6 family kinases which are tyrosine kinases. Brk is coded by 451 amino acids. Brk was identified from human normal melanocytes in the first place, and immediately after that, Brk was identified in breast cancer. Brk is highly expressed in a lot of tumors including breast cancer, ovarian cancer, colon cancer, pancreatic cancer, bladder cancer, esophageal cancer, gastric cancer, non-small-cell lung cancer, prostate cancer, oral squamous cell cancer, head and neck squamous cell cancer, melanoma, B-cell lymphoma, and T-cell lymphoma. In particular, Brk is a poor prognostic factor in breast cancer, prostate cancer, nasopharyngeal cancer, and non-small-cell lung cancer. In addition, it is thought that Brk plays important roles in tumorigenesis such as promotion of proliferation, migration, and invasion of cancer cells, and avoidance of cell death (see Non Patent Literatures 1 to 7).

Accordingly, it is thought that a compound which inhibits activation of Brk is useful for treating various types of cancer.

On the other hand, it has been described in Patent Literature 1 that, a compound of the following formula (IA) or a tautomer or pharmaceutically acceptable salt thereof is used for treating Syk and/or JAK related diseases such as cardiac disease, inflammatory disease, immune-related disease, and cell proliferative disorder.

The general formula (IA) is as follows:

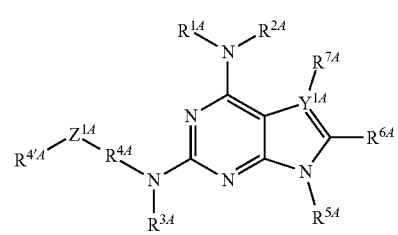

(IA)

(wherein:
$Y^{1A}$ is selected from the group consisting of N, CH and C;
$Z^{1A}$ is selected from the group consisting of a bond, —N($C_1$-$C_4$ alkyl)-, —$SO_2$—, and —CO— and the like;
$R^{1A}$ is selected from $C_{1-8}$ alkyl that may be substituted with hydrogen and substituents and the like;
$R^{2A}$ is selected from H, $C_{1-8}$ alkyl and the like;
$R^{3A}$ is selected from H, $C_{1-8}$ alkyl and the like;
$R^{4A}$ is selected from aryl and the like that may be substituted with 1 to 3 substituents, each of which is independently selected from $C_{1-8}$ alkoxy, amino, $C_{1-8}$ alkylcarbonyl, and aminocarbonyl $C_{1-8}$ alkoxy;
$R^{4'A}$ is selected from H, $C_{1-8}$ alkyl and the like;
$R^{5A}$ is selected from H, $C_{1-8}$ alkyl, $C_{3-8}$ cycloalkyl and the like;
$R^{6A}$ is selected from the group consisting of H, $C_{1-8}$ alkyl, halo hydroxyl, and oxo;
$R^{7A}$ is selected from the group consisting of H, $C_{1-8}$ alkyl, halo, and aryl and the like, each of aryl and heteroaryl may be substituted with halo, $C_{1-8}$ alkyl, $C_{1-8}$ alkoxy, cyano, amino, hydroxyl, heteroaryl; and the dashed line indicates a double bond or a single bond (the definition of groups is partly extracted)).

In addition, it has been described in Patent Literature 2 that a compound of the following formula (IB) is Toll Like Receptor agonist, and these compounds are used for treating autoimmune disease, cancer and the like.

The general formula (IB) is as follows:

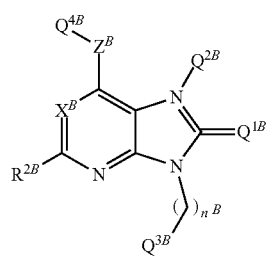

(IB)

(wherein:
$X^B$ is nitrogen or $CR^{8B}$;
and the dashed line indicates any double bond;
when $C=Q^{1B}$ is double bond, $Q^{1B}$ is oxygen or sulfur;
$Z^B$ is oxygen or sulfur or $NY^{5B}$, $Y^{5B}$ is hydrogen or alkyl and the like;

$Q^{2B}$ is substituted or unsubstituted aryl or heteroaryl and the like;
$Q^{4B}$ is hydrogen and the like;
$R^{2B}$ is hydrogen, alkyl, or $NY^{6B}Y^{7B}$, $Y^{6B}$ and $Y^{7B}$ are each independently hydrogen or substituted or unsubstituted aryl or heteroaryl and the like (the definition of groups is partly extracted)).

Further, it has been described in Patent Literature 3 that a compound of the following formula (IC) is p38 inhibitor, and these compounds are used for treating autoimmune disease, inflammatory disease and the like.

The general formula (IC) is as follows:

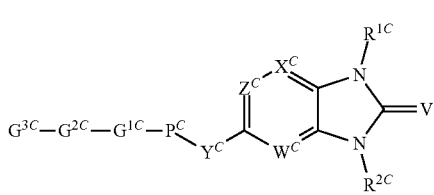

(IC)

(wherein:
$V^C$ is oxygen or sulfur;
$X^C$, $W^C$, and $Z^C$ are each independently $C(R^{4c})$ and nitrogen, but at least one of $X^C$, $W^C$, and $Z^C$ is nitrogen;
$Y^C$ is bond, —O—, or —NH— and the like;
$R^{1C}$ is optionally substituted aryl or heteroaryl and the like;
$R^{2C}$ is hydrogen, acyl, alkyl, or heterocycloalkyl and the like;
$R^{4C}$ is hydrogen, acyl, alkyl, alkylamino, or amino and the like;
$P^C$ is optionally substituted aryl, heteroaryl, or heterocycloalkyl that may be substituted with;
$G^{1C}$ and $G^{2C}$ are each independently represents bond, alkylene, —C(O)—, or —SO$_2$— and the like;
$G^{3C}$ is hydrogen or acyl and the like (the definition of groups is partly extracted).

CITATIONS LISTS

Patent Literatures

Patent Literature 1: WO 2009/131687 A
Patent Literature 2: WO 2007/142755 A
Patent Literature 3: WO 2007/015877 A Non Patent Literatures Non Patent Literature 1: Breast Cancer-Current and Alternative Therapeutic Modalities, pages 413-434, 2011
Non Patent Literature 2: Biochimica et Biophysica Acta, Vol. 1806, pages 66-73, 2010
Non Patent Literature 3: Cell Cycle, Vol. 8, pages 2728-2732, 2009
Non Patent Literature 4: Cancer Research, Vol. 73, pages 5810-5820, 2013
Non Patent Literature 5: Cancer Research, Vol. 73, pages 5426-5437, 2013
Non Patent Literature 6: OncoTargets and Therapy, Vol. 6, pages 183-188, 2013
Non Patent Literature 7: Journal of Translational Medicine, Vol. 11, 59, 2013

SUMMARY OF INVENTION

Technical Problems

An object of the present invention is to find out a compound useful as a therapeutic agent for Brk related diseases, particularly various cancer diseases by creating a compound having an inhibitory activity on Brk.

Solutions to Problems

The present inventors have carried out intensive studies to find a compound having an inhibitory activity on Brk in order to achieve the above-described object. As a result, the present inventors have found a compound represented by general formula (I) described below, and have completed the present invention.

In other words, the present invention relates to the followings:

[1] A compound represented by general formula (I):

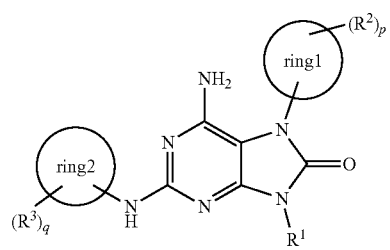

(I)

(wherein:
ring1 and ring2 each independently represent a $C_5$-10 carbocycle or a 5- to 10-membered heterocycle;
$R^1$ represents a C1-4 alkyl, a C2-4 alkenyl, a C2-4 alkynyl, a C3-6 cycloalkyl, or a 3- to 6-membered heterocycloalkyl, said C1-4 alkyl, C2-4 alkenyl, C2-4 alkynyl, C3-6 cycloalkyl, or 3- to 6-membered heterocycloalkyl may be substituted with a 1-5 halogen or a hydroxyl group,
$R^2$ represents a halogen, a C1-4 alkyl, $OR^4$, $NR^5R^6$, or an oxo, said C1-4 alkyl may be substituted with a 1-5 halogen,
$R^4$ represents a hydrogen atom, a C1-4 alkyl, or a benzene ring, said C1-4 alkyl or benzene ring is may be substituted with a 1-5 halogen;
$R^5$ and $R^6$ each independently represent a hydrogen atom or a C1-4 alkyl;
$R^3$ represents a halogen, a C1-4 alkyl, $OR^7$, $NR^8R^9$, $SO_2R^{10}$, $COR^{11}$, a benzene ring, a 4- to 6-membered heterocycle, or an oxo, said C1-4 alkyl may be substituted with a 1-5 substituents which are selected from the group consisting of a halogen, a hydroxyl group, a 4- to 6-membered heterocycle, and $CONR^{12}R^{13}$;
$R^7$ represents a hydrogen atom or a C1-4 alkyl, said C1-4 alkyl may be substituted with a 1-5 halogen or $NR^{14}R^{15}$;
$R^8$ and $R^9$ each independently represent a hydrogen atom, a C1-4 alkyl, or acetyl;
$R^{10}$ represents a C1-4 alkyl or $NR^{16}R^{17}$;
$R^{11}$ represents a hydroxyl group, a C1-4 alkyl, $NR^{18}R^{19}$, or a 4- to 6-membered heterocycle, said 4- to 6-membered heterocycle may be substituted with a 1-5 substituents which are selected from the group consisting of a halogen, a hydroxyl group and a C1-4 alkyl;

$R^{12}$, $R^{13}$, $R^{14}$, $R^{15}$, $R^{16}$ and $R^{17}$ each independently represent a hydrogen atom or a C1-4 alkyl;

$R^{18}$ and $R^{19}$ each independently represent a hydrogen atom, a C1-4 alkyl, or a 4- to 6-membered heterocycle, said C1-4 alkyl may be substituted with a 1-5 hydroxyl group, a C1-3alkoxy, or $NR^{20}R^{21}$;

$R^{20}$ and $R^{21}$ each independently represent a hydrogen atom or a C1-4 alkyl;

p represents an integer of 0 to 7;

q represents an integer of 0 to 7;

provided that when p and q each represent an integer of 2 or more, $R^2$ and $R^3$ each independently may be the same or different);

a salt thereof, an N-oxide thereof, a solvate thereof, or a prodrug of any of these;

[2] The compound according to the above item [1], a salt thereof, an N-oxide thereof, a solvate thereof, or a prodrug of any of these, wherein $R^1$ is isopropyl, tert-butyl, isobutyl, a C3-6 cycloalkyl, or a 3- to 6-membered heterocycloalkyl that may be substituted with a 1-5 halogen or a hydroxyl group;

[3] The compound according to the above items [1] or [2], a salt thereof, an N-oxide thereof, a solvate thereof, or a prodrug of any of these, wherein ring1 is a 9- to 10-membered nitrogen-containing bicyclic aromatic heterocyclic;

[4] The compound according to any one of the above items [1] to [3], a salt thereof, an N-oxide thereof, a solvate thereof, or a prodrug of any of these, wherein ring2 is a benzene ring;

[5] The compound according to any one of the above items [1] to [4], a salt thereof, an N-oxide thereof, a solvate thereof, or a prodrug of any of these, wherein q is an integer of 1 or more, $R^3$ is at least one a halogen, a C1-3 alkoxy, $SO_2R^{10}$, or $COR^{11}$;

[6] The compound according to the above item [1], which is represented by general formula (I-1):

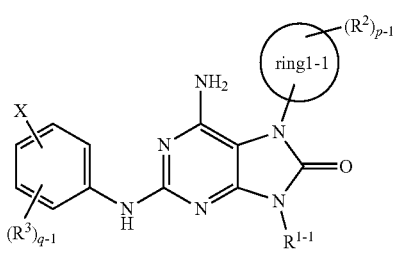

(wherein, ring1-1 represents indol ring or indazole ring, $R^{1-1}$ represents isopropyl, tert-butyl, cyclobutyl, cyclopentyl, difluorocyclopentyl, oxetanyl, or tetrahydrofuranyl, X represents a halogen, p-1 represents an integer of 0 to 6, q-1 represents an integer of 0 to 4, the other symbols represent the same meanings as symbols set forth in the above item [1]);

a salt thereof, an N-oxide thereof, a solvate thereof, or a prodrug of any of these;

[7] The compound according to the above item [1], which is represented by general formula (I-1'):

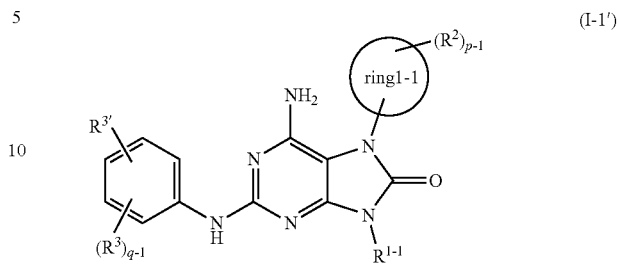

(wherein, $R^{3'}$ represents $SO_2R^{10}$ or $COR^{11}$, the other symbols represent the same meanings as symbols set forth in the above item [1] or [6]);

a salt thereof, an N-oxide thereof, a solvate thereof, or a prodrug of any of these;

[8] A compound according to the above item [1], which is:
(1) 6-amino-7-(7-fluoro-1H-indazole-4-yl)-2-{[2-fluoro-4-(methylsulfonyl)phenyl]amino}-9-isopropyl-7,9-dihydro-8H-purine-8-one;
(2) 6-amino-7-(7-chloro-1H-indazol-4-yl)-2-{[2-fluoro-4-(methylsulfonyl)phenyl]amino}-9-isopropyl-7,9-dihydro-8H-purine-8-one;
(3) 6-amino-7-(6,7-difluoro-1H-indazol-4-yl)-2-{[2-fluoro-4-(methylsulfonyl)phenyl]amino}-9-isopropyl-7,9-dihydro-8H-purine-8-one;
(4) 6-amino-7-(7-fluoro-1H-indazol-4-yl)-2-{[2-fluoro-4-(methylsulfonyl)phenyl]amino}-9-(2-methyl-2-propanyl)-7,9-dihydro-8H-purine-8-one;
(5) 2-[(4-acetyl-2-fluorophenyl)amino]-6-amino-7-(1H-indazol-4-yl)-9-isopropyl-7,9-dihydro-8H-purine-8-one;
(6) 6-amino-9-cyclopentyl-2-{[2-fluoro-4-(methylsulfonyl)phenyl]amino}-7-(1H-indazol-4-yl)-7,9-dihydro-8H-purine-8-one;
(7) 6-amino-9-cyclobutyl-2-{[2-fluoro-4-(methylsulfonyl)phenyl]amino}-7-(1H-indazol-4-yl)-7,9-dihydro-8H-purine-8-one;
(8) 6-amino-2-{[2-fluoro-4-(methylsulfonyl)phenyl]amino}-7-(1H-indazol-4-yl)-9-(2-met-2-propanyl)-7,9-dihydro-8H-purine-8-one;
(9) 6-amino-2-{[2-fluoro-4-(methylsulfonyl)phenyl]amino}-9-isopropyl-7-(7-methyl-1H-indazol-4-yl)-7,9-dihydro-8H-purine-8-one;
(10) 6-amino-9-(3,3-difluorocyclopentyl)-2-{[2-fluoro-4-(methylsulfonyl)phenyl] amino}-7-(1H-indazol-4-yl)-7,9-dihydro-8H-purine-8-one;
(11) 6-amino-7-(7-chloro-1H-indazol-4-yl)-9-isopropyl-2-{[2-methoxy-4-(methylsulfonyl)phenyl] amino}-7,9-dihydro-8H-purine-8-one;
(12) 6-amino-7-(7-fluoro-1H-indazol-4-yl)-2-{[2-methoxy-4-(methylsulfonyl)phenyl]amino}-9-(2-methyl-2-propanyl)-7,9-dihydro-8H-purine-8-one;
(13) 6-amino-2-{(2-fluoro-4-(methylsulfonyl)phenyl] amino}-7-(1H-indazol-6-yl)-9-(tetrahydro-3-furanyl)-7,9-dihydro-8H-purine-8-one;
(14) 6-amino-9-cyclopentyl-2-{(2-fluoro-4-(methylsulfonyl)phenyl]amino}-7-(3-hydroxyphenyl)-7,9-dihydro-8H-purine-8-one;
(15) 6-amino-2-{[2,3-difluoro-4 (methylsulfonyl)phenyl] amino}-7-(7-fluoro-1H-indazol-4-yl)-9-isopropyl-7,9-dihydro-8H-purin-8-one;

(16) 6-amino-2-{[2,5-difluoro-4-(methylsulfonyl)phenyl] amino}-7-(7-fluoro-1H-indazol-4-yl)-9-isopropyl-7,9-dihydro-8H-purine-8-one;
(17) 6-amino-7-(3-amino-4-fluorophenyl)-2-{[2-fluoro-4-(methylsulfonyl)phenyl] amino}-9-isopropyl-7,9-dihydro-8H-purine-8-one;
(18) 6-amino-7-(1-benzofuran-5-yl)-2-{[2-fluoro-4-(methylsulfonyl)phenyl]amino}-9-isopropyl-7,9-dihydro-8H-purine-8-one;
(19) 6-amino-2-{[2-fluoro-4-(methylsulfonyl)phenyl] amino}-7-(1H-indazol-4-yl)-9-(1,1,1-trifluoro-2-propanyl)-7,9-dihydro-8H-purine-8-one;
(20) 6-amino-9-[(2S)-2-butanyl]-7-(7-fluoro-1H-indazol-4-yl)-2-{[2-fluoro-4-(methylsulfonyl)phenyl] amino}-7,9-dihydro-8H-purine-8-one;
(21) 6-amino-7-(4-chloro-3-hydroxyphenyl)-9-(3,3-difluorocyclopentyl)-2-{[2-fluoro-4-(1-piperazinyl carbonyl) phenyl]amino}-7,9-dihydro-8H-purine-8-one;
(22) 6-amino-7-(1H-indol-5-yl)-9-isopropyl-2-[(2-methyl-1-oxo-2,3-dihydro-1H-isoindole-5-yl)amino]-7,9-dihydro-8H-purine-8-one;
(23) 6-amino-2-[(1,3-dimethyl-1H-pyrazole-4-yl)amino]-7-(1H-indole-6-yl)-9-isopropyl-7,9-dihydro-8H-purine-8-one;
(24) 4-{[(6-amino-7-(1H-indole-5-yl)-9-isopropyl-8-oxo-8, 9-dihydro-7H-purine-2-yl]amino}-3-fluoro-N,N-dimethylbenzamide;
(25) 6-amino-9-cyclopentyl-7-(3-hydroxyphenyl)-2-({4-[2-(1-pyrrolidinyl)ethyl]phenyl}amino)-7,9-dihydro-8H-purine-8-one;
(26) 4-{[(6-amino-9-cyclopentyl-7-(3-hydroxyphenyl)-8-oxo-8,9-dihydro-7H-purine-2-yl]amino}-3-methoxy-N, N-dimethylbenzamide;
(27) 4-{[(6-amino-7-(4-chloro-3-hydroxyphenyl)-9-isopropyl-8-oxo-8,9-dihydro-7H-purine-2-yl]amino}-N-[2-(dimethylamino) ethyl]-3-fluorobenzamide;
(28) 6-amino-9-cyclopentyl-2-{[2-fluoro-4-(4-morpholinylcarbonyl)phenyl]amino}-7-(3-hydroxyphenyl)-7,9-dihydro-8H-purine-8-one;
(29) 4-{[6-amino-9-cyclopentyl-7-(3-hydroxyphenyl)-8-oxo-8,9-dihydro-7H-purine-2-yl]amino}benzamide;
(30) 6-amino-9-cyclopentyl-7-(3-hydroxyphenyl)-2-{[4-(4-morpholinyl)phenyl]amino}-7,9-dihydro-8H-purine-8-one;
(31) 4-{[6-amino-9-cyclopentyl-7-(3-hydroxyphenyl)-8-oxo-8,9-dihydro-7H-purine-2-yl]amino}-3-fluoro-N-(2-hydroxyethyl)benzamide;
(32) 6-amino-2-({2-fluoro-4-[(4-hydroxy-1-piperidinyl) carbonyl]phenyl}amino)-7-(1H-indole-5-yl)-9-(tetrahydro-3-furanyl)-7,9-dihydro-8H-purine-8-one;
(33) 5-{[6-amino-7-(1H-indole-5-yl)-9-isopropyl-8-oxo-8, 9-dihydro-7H-purine-2-yl] amino}-N,N-dimethyl-2-pyridinecarboxamide;
(34) 6-amino-7-(1H-indole-5-yl)-9-isopropyl-2-[(2-methyl-4-oxo-4H-chromene-7-yl) amino]-7,9-dihydro-8H-purine-8-one;
(35) 6-amino-7-(1H-indole-5-yl)-9-isopropyl-2-[(1-oxo-1, 3-dihydro-2-benzofuran-5-yl) amino]-7,9-dihydro-8H-purine-8-one;
(36) 7-{[6-amino-7-(1H-indole-5-yl)-9-isopropyl-8-oxo-8, 9-dihydro-7H-purine-2-yl] amino}-4-methyl-2H-1,4-benzoxazine-3(4H)-one, or
(37) 4-{[6-amino-7-(1H-indole-5-yl)-8-oxo-9-(tetrahydro-3-furanyl)-8,9-dihydro-7H-purine-2-yl]amino}-3-fluorobenzenesulfonamide;
a salt thereof, an N-oxide thereof, a solvate thereof, or a prodrug of any of these;

[9] A pharmaceutical composition comprising the compound represented by general formula (I) according to the above item [1], a salt thereof, an N-oxide thereof, a solvate thereof or a prodrug of any of these as an active ingredient;
[10] The composition according to the above item [9], which is a Brk inhibitor;
[11] The composition according to the above item [9], which is an agent for treating cancer;
[12] The composition according to the above item [11], wherein the cancer is breast cancer, ovarian cancer, large bowel cancer, lung cancer, prostate cancer, head and neck cancer, lymphoma, brain tumor, glioma, pituitary adenoma, uveal malignant melanoma, meningioma, thymoma, mesothelioma, esophageal cancer, gastric cancer, duodenal cancer, hepatocellular cancer, bile duct cancer, gallbladder cancer, pancreatic cancer, renal cell cancer, renal pelvis-ureteral cancer, bladder cancer, penile cancer, testicular cancer, uterine cancer, vaginal cancer, vulvar cancer, skin cancer, malignant bone tumor, soft tissue sarcoma, chondrosarcoma, leukemia, myelodysplastic syndrome, and multiple myeloma;
[13] A preventive and/or therapeutic agent for Brk related disease comprising the compound represented by general formula (I) according to the above item [1], a salt thereof, an N-oxide thereof, a solvate thereof, or a prodrug comprising the same as an active ingredient;
[14] The therapeutic agent according to the above item [13], wherein Brk-related disease is cancer;
[15] The therapeutic agent according to the above item [14], wherein the cancer is breast cancer, ovarian cancer, large bowel cancer, lung cancer, prostate cancer, head and neck cancer, lymphoma, brain tumor, glioma, pituitary adenoma, uveal malignant melanoma, meningioma, thymoma, mesothelioma, esophageal cancer, gastric cancer, duodenal cancer, hepatocellular cancer, bile duct cancer, gallbladder cancer, pancreatic cancer, renal cell cancer, renal pelvis-ureteral cancer, bladder cancer, penile cancer, testicular cancer, uterine cancer, vaginal cancer, vulvar cancer, skin cancer, malignant bone tumor, soft tissue sarcoma, chondrosarcoma, leukemia, myelodysplastic syndrome, or multiple myeloma;
[16] A medicament comprising the compound represented by general formula (I) according to the above item [1], a salt thereof, an N-oxide thereof, a solvate thereof, or a prodrug of any of these in combination with at least one kind selected from an alkylating agent, an antimetabolite, an anticancer antibiotic, a plant-derived preparation, a hormone preparation, a platinum compound, a immunomodulator, a topoisomerase inhibitor, a biological response modifier, a kinase inhibitor, an immune checkpoint inhibitor, a histone deacetylase (HDAC) inhibitor, a proteasome inhibitor, an anti-CD20 antibody, an anti-HER2 antibody, an anti-EGFR antibody, and an anti-VEGF antibody;
[17] A method for treating cancer comprising administering an effective amount of the compound represented by general formula (I) according to the above item [1], a salt thereof, an N-oxide thereof, a solvate thereof, or a prodrug of any of these to a patient in need of the treatment of cancer;
[18] The compound represented by general formula (I) according to the above item [1], a salt thereof, an N-oxide thereof, a solvate thereof, or a prodrug of any of these for treating cancer;
[19] Use of the compound represented by general formula (I) according to the above item [1], a salt thereof an N-oxide thereof, a solvate thereof, or a prodrug of any of these for the manufacture of an agent for treating cancer; and

[20] A method for inhibiting Brk comprising administering an effective amount of the compound represented by general formula (I) according to the above item [1], a salt thereof, an N-oxide thereof, a solvate thereof; or a prodrug of any of these to a patient in need of the inhibition of Brk.

Advantageous Effects of Invention

The compound of the present invention has a Brk inhibitory activity and kinases selectivity, and therefore, is a therapeutic agent with excellent safety for diseases in which Brk involves, for example, cancer.

DESCRIPTION OF EMBODIMENTS

The present invention is described in details hereinbelow.

In the present invention, a "C5-10 carbocycle" refers to a C5-10 monocyclic or bicyclic saturated carbocycle, a C5-10 monocyclic or bycyclic unsaturated carbocycle, and a C5-10 monocyclic or bicyclic partially unsaturated carbocycle and the like. A "C5-10 carbocycle" refers to, for example, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, and perhydronaphthalene and the like.

In the present invention, a "5- to 10-membered heterocycle" refers to a 5- to 10-membered monocyclic or bicyclic saturated heterocycle, a 5- to 10-membered monocyclic or bicyclic unsaturated heterocycle, and a 5- to 10-membered monocyclic or bicyclic partially unsaturated heterocycle and the like. A "5- to 10-membered heterocycle" refers to, for example, pyrrolidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridine, naphthyridine, quinoxaline, quinazoline, cinnoline, benzoxazole, benzothiazole, benzimidazole, benzodioxole, benzoxathiol, chromene, benzofurazan, benzothiadiazole, benzoxadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepinc, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidinc), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazinc, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, tetrahydrotriazolopyrazine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dioxaindane, benzodioxane, thiochroman, dihydrobenzodioxin, dihydrobenzoxatyne, chromane, pyrazolopyrimidine, imidazopyridazine, imidazopyridine, pyrrolopyridine, imidazopyrazine, pyrazolopyridine, imidazopyridine, triazolopyridine, benzopyran, phthalane, dihydrobenzoxazine, azaindole ring and the like.

In the present invention, a "C1-4 alkyl group" refers to, for example, methyl, ethyl, n-propyl, isopropyl, n-butyl, sec-butyl, tert-butyl, and isobutyl groups.

In the present invention, a "C2-4 alkenyl group" refers to, for example, vinyl, 1-propenyl, 2-propenyl, 1-butenyl, 2-butenyl, 3-butenyl groups and the like.

In the present invention, a "C2-4 alkynyl group" refers to, for example, ethinyl, 1-propynyl, 2-propynyl, 1-butynyl, 2-butynyl, 3-butynyl groups and the like.

In the present invention, a "C3-6 cycloalkyl group" refers to cyclopropyl, cyclobutyl, cyclopentyl, and cyclohexyl groups.

In the present invention, "3- to 6-membered heterocycloalkyl group" refers to oxiranyL thiiranyl, aziridinyl, oxetanyl, thietanyl, azetidinyl, tetrahydrofiranyl, tetrahydrothiophenyl, pyrrolidinyl, tetrahydropyranyl, tetrahydrothiopyranyl, piperidinyl group and the like.

In the present invention, a "halogen" refers to fluorine, chlorine, bromine, and iodine.

In the present invention, a "4- to 6-membered heterocycle" refers to a 4- to 6-membered monocyclic saturated heterocycle, a 4- to 6-membered monocyclic unsaturated heterocycle, and a 4-6 membered monocyclic partially unsaturated heterocycle and the like. A "4- to 6-membered heterocycle" refers to, for example, oxetane, thietane, azetidine, tetrahydrofuran, tetrahydrothiophene, tetrahydropyran, tetrahydrothiopyran, morpholine, thiomorpholine, pyrrolidine, pyrrole, imidazole, triazole, tetrazole, pyrazole, pyridine, piperidine, piperazine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, and thiadiazine rings and the like.

In the present invention, a "C1-3 alkoxy group" refers to methoxy, ethoxy, n-propoxy, and isopropoxy groups.

In the present invention, a "9- to 10-membered nitrogen-containing bicyclic aromatic heterocycle" refers to 9- to 10-membered bicyclic aromatic heterocyclic ring that may be contained at least one nitrogen atom besides carbon atoms and may be optionally contained 1-3 hetero atoms selected from a nitrogen atom, an oxygen atom and a sulfur atom. A "9- to 10-membered nitrogen-containing bicyclic aromatic heterocycle" refers to, for example, indole, indazole, benzotriazole, azaindole, pyrazolopyrimidine, benzimidazole, benzothiazole, benzooxazole, benzooxadiazole, benzothiadiazole, quinoline, isoquinoline, purine, phthalazine, pteridine, naphthyridine, quinoxaline, quinazoline, and cinnoline rings and the like.

In the present invention, ring1 is preferably a 9- to 10-membered nitrogen-containing bicyclic aromatic heterocycle, is more preferably an indole, indazole, benzotriazole, azaindole, pyrazolopyrimidine, benzoimidazole, benzothiazole, benzoxazole, benzoxadiazole, benzothiadiazole, quinoline, isoquinoline, purine, phthalazine, pteridine, naphthyridine, quinoxaline, quinazoline, or cinnoline rings, is furthermore preferably a an indole, indazole, benzotriazole, azaindole, pyrazolopyrimidine, benzimidazole, benzothiazole, benzooxazole, benzooxadiazole, or benzothiadiazole rings, and is especially preferably an indole or indazole ring.

And ring1 is also preferably a benzene, or benzofuran ring.

In the present invention, ring2 is preferably a benzene, pyrazole, imidazole, oxazole, thiazole, pyridine, pyrimidine, pyrazine, isoindoline, or pyridazine rings, and is more preferably a benzene ring.

In the present invention, $R^1$ is preferably isopropyl, tert-butyl, isobutyl, C3-6 cycloalkyl, or 3- to 6-membered heterocycloalkyl group that may be substituted with a halogen or hydroxyl group, is more preferably isopropyl, tert-butyl, cyclobutyl, cyclopentyl, difluorocyclopentyl, oxetanyl, or tetrahydrofuranyl group, is furthermore preferably a isopropyl, tert-butyl, cyclopentyl, or difluorocyclopentyl group, and is especially preferably isopropyl or tert-butyl group.

In the present invention, $R^2$ is preferably a halogen, methyl, difluoromethyl, trifluoromethyl, methoxy, difluoromethoxy, phenoxy, hydroxyl group, amino group, or oxo, and is the more preferably a halogen or hydroxyl group.

In the present invention, $R^3$ is preferably a halogen, C1-4 alkyl, C1-3 alkoxy, $SO_2R^{10}$, or $COR^{11}$, and is more preferably a halogen, $SO_2R^{10}$, or $COR^{11}$. $R^3$ is furthermore preferably a halogen, or $R^3$ is furthermore preferably $SO_2R^{10}$ or $COR^{11}$.

In the present invention, $R^4$ is preferably a hydrogen atom, methyl, difluoromethyl, or benzene ring.

In the present invention, $R^5$ and $R^6$ are preferably each independently a hydrogen atom, methyl, or ethyl, and is preferably a hydrogen atom.

In the present invention, $R^7$ is preferably a hydrogen atom, methyl, difluoromethyl, or dimethylaminomethyl.

In the present invention, $R^8$ and $R^9$ are preferably each independently a hydrogen atom or acetyl.

In the present invention, $R^{10}$ is preferably a C1-4 alkyl, dimethylamino, methylamino, or amino, is preferably a C1-4 alkyl, and is especially preferably a methyl.

In the present invention, $R^{11}$ is preferably a hydroxyl group, C1-4 alkyl, amino, methylamino, dimethylamino, dimethylaminoethylamino($-NHCH_2CH_2NMe_2$), hydroxyethylamino($-NHCH_2CH_2OH$), hydroxyethylmethylamino($-NMeCH_2CH_2OH$), methoxyethylamino($-NHCH_2CH_2OMe$), methoxyethylmethylamino($-NMeCH_2CH_2OMe$), 2-hydroxy-2-methylpropylamino($-NHCH_2CMe(OH)(Me)$, piperidine, piperazine, methylpiperazine, pyrrolidine, or azetidine, is more preferably a C1-4 alkyl, and is especially preferably methyl.

In the present invention, $R^{12}$, $R^{13}$, $R^{14}$, $R^{15}$, $R^{16}$, and $R^{17}$ are preferably each independently a hydrogen atom or methyl.

In the present invention, $R^{18}$ and $R^{19}$ are preferably each independently a hydrogen atom, methyl, oxetane, dimethylaminoethyl($-CH_2CH_2NMe_2$), hydroxyethyl($-CH_2CH_2OH$), methoxyethyl($-CH_2CH_2OMe$), 2-hydroxy-2-methylpropyl($-CH_2CMe(OH)(Me)$).

In the present invention, $R^{20}$ and $R^{21}$ are preferably each independently a hydrogen atom or methyl.

In the present invention, p is preferably an integer of 0 to 4, and is more preferably an integer of 0 to 2.

In the present invention, q is preferably an integer of 0 to 4, and is more preferably an integer of 0 to 3.

In the present invention, a 9- to 10-membered nitrogen-containing bicyclic aromatic heterocycle is preferably an indole, indazole, benzotriazole, azaindole, pyrazolopyrimidine, benzoimidazole, benzothiazole, benzoxazole, benzoxadiazole, benzothiadiazole, quinoline, isoquinoline, purine, phthalazine, pteridine, naphthyridine, quinoxaline, quinazoline, or cinnoline rings, is more preferably an indole, indazole, benzotriazole, azaindole, pyrazolopyrimidine, benzoimidazole, benzothiazole, benzoxazole, benzoxadiazole, or benzothiadiazole ring, and is furthermore preferably an indole or indazole ring.

In the present invention, $R^{1-1}$ is preferably an isopropyl, tert-butyl, cyclopentyl, or difluorocyclopentyl group, and is more preferably an isopropyl or tert-butyl group.

In the present invention, X is preferably a fluorine or chlorine, and is more preferably fluorine.

In the present invention, general formula (I) is preferably a combination of the above-described preferable meaning of each of ring1, ring2, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, p, and q.

In the present invention, general formula (I) is preferably a compound represented by general formula (I-a):

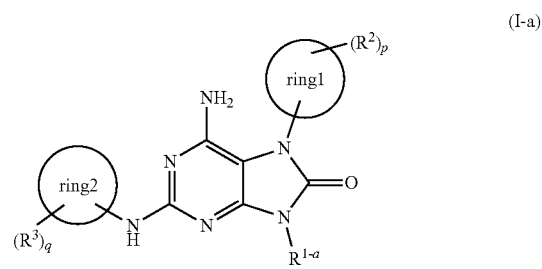

(I-a)

(wherein, $R^{1-a}$ represents an isopropyl, tert-butyl, isobutyl, a C3-6 cycloalkyl, or a 3- to 6-membered heterocycloalkyl that may be substituted with a 1-5 halogen or a hydroxyl group, and the other symbols represent the same meanings as symbols set forth in the above item [1]), a salt thereof, an N-oxide thereof, a solvate thereof, or a prodrug of any of these.

In the present invention, another aspect of general formula (I) is preferably a compound represented by general formula (I-b):

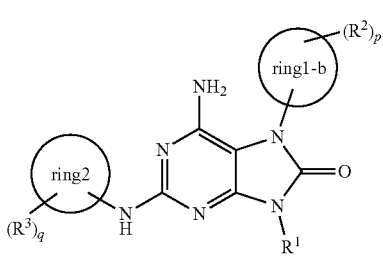
(I-b)

(wherein, ring1-b represents a 9- to 10-membered nitrogen-containing bicyclic aromatic heterocycle, and the other symbols represent the same meanings as symbols set forth in the above item [1]), a salt thereof, an N-oxide thereof, a solvate thereof, or a prodrug of any of these.

In the present invention, another aspect of general formula (I) is preferably a compound represented by general formula (I-c):

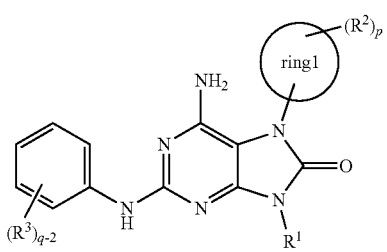
(I-c)

(wherein, q-2 represents an integer of 0 to 5, and the other symbols represent the same meanings as symbols set forth in the above item [1]), a salt thereof, an N-oxide thereof, a solvate thereof, or a prodrug of any of these.

In the present invention, general formula (I) is more preferably a compound represented by general formula (I-d):

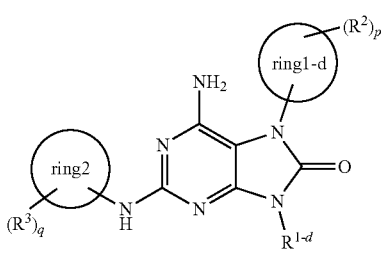
(I-d)

(wherein, $R^{1-d}$ represents an isopropyl, tert-butyl, isobutyl, a C3-6 cycloalkyl, or a 3- to 6-membered heterocycloalkyl that may be substituted with a 1-5 halogen or hydroxyl group;
ring1-d represents a 9- to 10-membered nitrogen-containing bicyclic aromatic heterocycle, and the other symbols represent the same meanings as symbols set forth in the above item [1]), a salt thereof, an N-oxide thereof, a solvate thereof, or a prodrug of any of these.

In the present invention, another aspect of general formula (I) is preferably a compound represented by general formula (I-e):

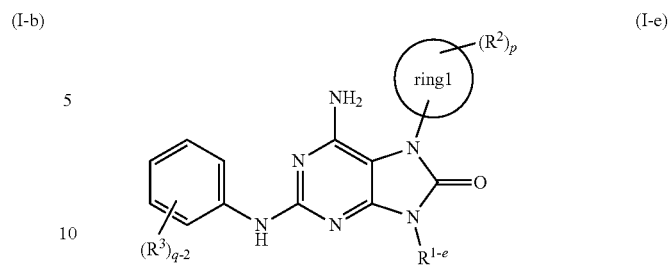
(I-e)

(wherein, $R^{1-e}$ represents an isopropyl, tert-butyl, isobutyl, a C3-6 cycloalkyl, or a 3- to 6-membered heterocycloalkyl that may be substituted with a 1-5 halogen or hydroxyl group;
q-2 represents an integer of 0 to 5, and the other symbols represent the same meanings as symbols set forth in the above item [1]), a salt thereof, an N-oxide thereof a solvate thereof, or a prodrug of any of these.

In the present invention, another aspect of general formula (I) is preferably a compound represented by general formula (I-f):

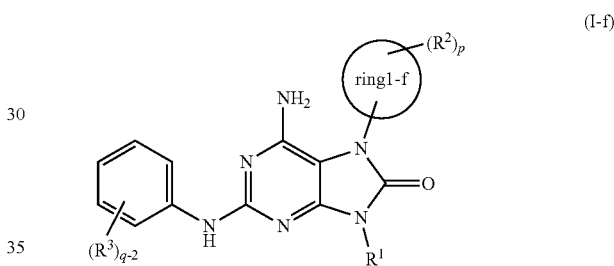
(I-f)

(wherein, ring1-f represents a 9- to 10-membered nitrogen-containing bicyclic aromatic heterocycle;
q-2 represents an integer of 0 to 5, and the other symbols represent the same meanings as symbols set forth in the above item [1]), a salt thereof, an N-oxide thereof, a solvate thereof, or a prodrug of any of these.

In the present invention, general formula (I) is furthermore preferably a compound represented by general formula (I-g):

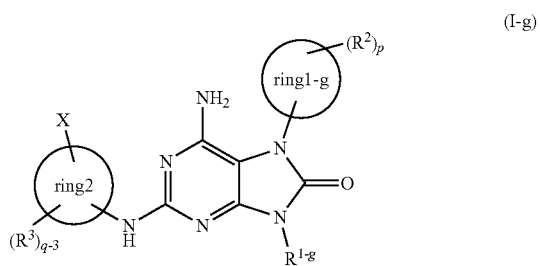
(I-g)

(wherein, $R^{1-g}$ represents an isopropyl, tert-butyl, isobutyl, a C3-6 cycloalkyl, or a 3- to 6-membered heterocycloalkyl that may be substituted with a 1-5 halogen or hydroxyl group;
ring1-g represents a 9- to 10-membered nitrogen-containing bicyclic aromatic heterocycle, and the other symbols represent the same meanings as symbols set forth in the above item [1] or [6]), a salt thereof, an N-oxide thereof, a solvate thereof, or a prodrug of any of these, and general formula (I) is more preferably a compound represented by general formula (I-g'):

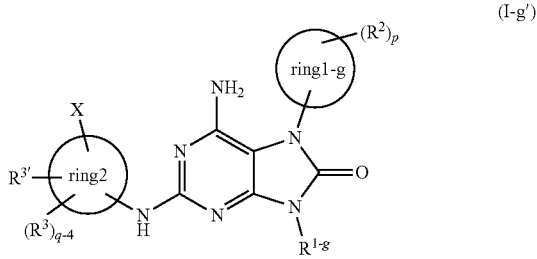

(I-g')

(wherein, $R^{1-g}$ represents an isopropyl, tert-butyl, isobutyl, C3-6 cycloalkyl, or 3- to 6-membered heterocycloalkyl that may be substituted with a 1-5 halogen or hydroxyl group; ring1-g represents a 9- to 10-membered nitrogen-containing bicyclic aromatic heterocycle, $R^{3'}$ represents $SO_2R^{10}$ or $COR^{11}$, q-4 represents an integer of 0 to 5, and the other symbols represent the same meanings as symbols set forth in the above item [1] or [6]), a salt thereof, an N-oxide thereof, a solvate thereof, or a prodrug of any of these.

In the present invention, another aspect of general formula (I) is furthermore preferably a compound represented by general formula (I-h):

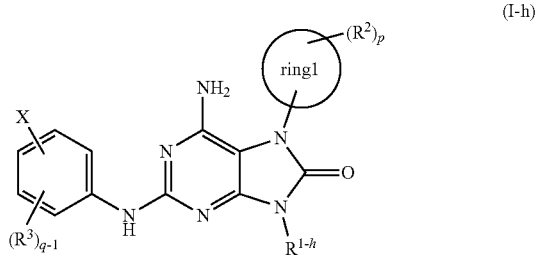

(I-h)

(wherein, $R^{1-h}$ represents an isopropyl, tert-butyl, isobutyl, a C3-6 cycloalkyl, or a 3- to 6-membered heterocycloalkyl that may be substituted with a 1-5 halogen or hydroxyl group, and the other symbols represent the same meanings as symbols set forth in the above item [1] or [6]), a salt thereof, an N-oxide thereof, a solvate thereof, or a prodrug of any of these, and general formula (I) is more preferably a compound represented by general formula (I-h'):

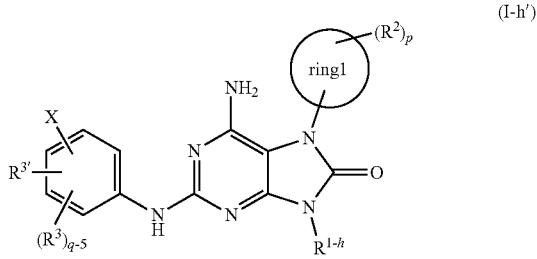

(I-h')

(wherein, $R^{1-h}$ represents an isopropyl, tert-butyl, isobutyl, a C3-6 cycloalkyl, or a 3- to 6-membered heterocycloalkyl that may be substituted with a 1-5 halogen or hydroxyl group, $R^{3'}$ represents $SO_2R^{10}$ or $COR^{11}$, q-5 represents an integer of 0 to 3, and the other symbols represent the same meanings as symbols set forth in the above item [1] or [6]), a salt thereof, an N-oxide thereof, a solvate thereof, or a prodrug of any of these.

In the present invention, another aspect of general formula (I) is furthermore preferably a compound represented by general formula (I-j):

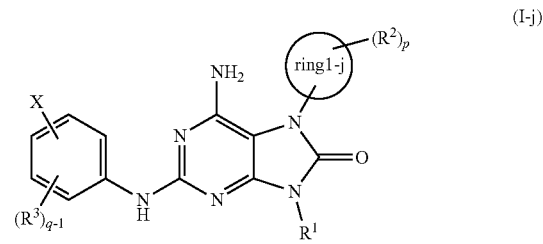

(I-j)

(wherein, ring1-j represents a 9- to 10-membered nitrogen-containing bicyclic aromatic heterocycle, and the other symbols represent the same meanings as symbols set forth in the above item [1] or [6]), a salt thereof, an N-oxide thereof, a solvate thereof, or a prodrug of any of these, and general formula (I) is more preferably a compound represented by general formula (I-j'):

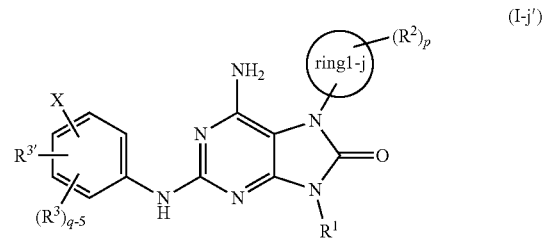

(I-j')

(wherein, ring1-j represents a 9- to 10-membered nitrogen-containing bicyclic aromatic heterocycle, $R^{3'}$ represents $SO_2R^{10}$ or $COR^{11}$, q-5 represents an integer of 0 to 3, and the other symbols represent the same meanings as symbols set forth in the above item [1] or [6]), a salt thereof, an N-oxide thereof, a solvate thereof, or a prodrug of any of these.

In the present invention, another aspect of general formula (I) is furthermore preferably a compound represented by general formula (I-k):

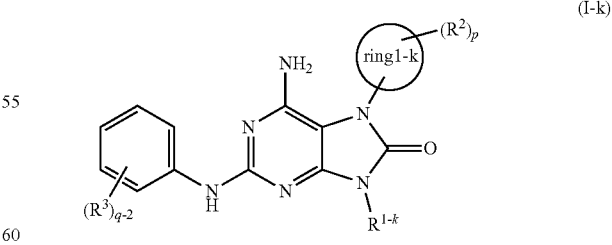

(I-k)

(wherein, $R^{1-k}$ represents an isopropyl, tert-butyl, isobutyl, a C3-6 cycloalkyl, or a 3- to 6-membered heterocycloalkyl that may be substituted with a 1-5 halogen or hydroxyl group, ring1-k represents a 9- to 10-membered nitrogen-containing bicyclic aromatic heterocycle, q-2 represents an integer of 0 to 5, and the other symbols represent the same meanings as symbols set forth in the above item [1]), a salt thereof an N-oxide thereof, a solvate thereof, or a prodrug of any of these, and general formula (I) is more preferably a compound represented by general formula (I-k'):

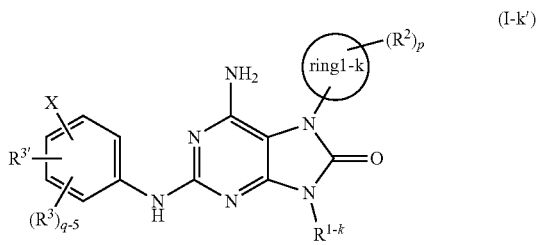

(wherein, $R^{1-k}$ represents an isopropyl, tert-butyl, isobutyl, a C3-6 cycloalkyl, or a 3- to 6-membered heterocycloalkyl that may be substituted with a 1-5 halogen or hydroxyl group;
ring1-k represents a 9- to 10-membered nitrogen-containing bicyclic aromatic heterocycle, $R^{3'}$ represents $SO_2R^{10}$ or $COR^{11}$, q-5 represents an integer of 0 to 3, and the other symbols represent the same meanings as symbols set forth in the above item [1] or [6]), a salt thereof, an N-oxide thereof, a solvate thereof, or a prodrug of any of these.

In the present invention, general formula (I) is especially preferably a compound represented by general formula (I-1):

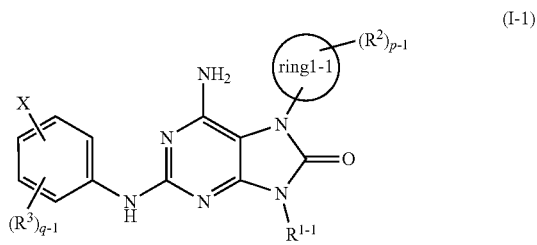

(wherein, all symbols represent the same meanings as symbols set forth in the above item [1] or [6]), a salt thereof, an N-oxide thereof, a solvate thereof, or a prodrug of any of these. In the general formula (I-1), q-1 is more preferably 1 or more, and at least one of $R^3$ represents $SO_2R^{10}$ or $COR^{11}$.

In the present invention, another aspect of general formula (I) is especially preferably a compound represented by general formula (I-1'):

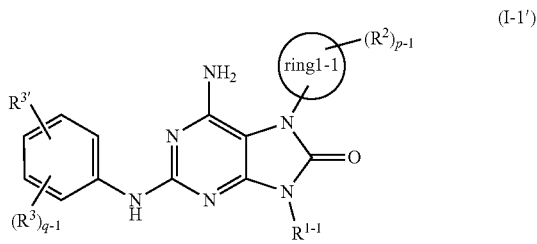

(wherein, $R^{3'}$ represents $SO_2R^{10}$ or $COR^{11}$, and the other symbols represent the same meanings as symbols set forth in the above item [1] or [6]), a salt thereof, an N-oxide thereof, a solvate thereof, or a prodrug of any of these. In the general formula (I-1'), q-1 is more preferably 1 or more, at least one of $R^3$ represents a halogen.

In the present invention, another aspect of general formula (I) is preferably general formula selected from the group of the above-described general formula (I-a), general formula (I-b), general formula (I-c), general formula (I-d), general formula (I-e), and general formula (I-f), is each independently, when R3 is two or more, at least two of these R3 represent a halogen and $SO_2R^{10}$, or a halogen and $COR^{11}$.

In the present invention, another aspect of general formula (I) is the most preferably the compounds of the present invention described in the following Examples 1, the compounds of the present invention described in Examples 2-1 to Examples 2-2, the compounds of the present invention described in Examples 3 to Examples 4, or the compounds of the present invention described in Examples 5-1 to Examples 5-32, a salt thereof, an N-oxide thereof, a solvate thereof, or a prodrug of any of these.

In the present invention, unless otherwise specifically indicated, all isomers are included in the present invention. For example, an alkyl group, an alkenyl group, an alkynyl group, an alkoxy group and the like include linear and branched ones. In addition, all of isomers due to ring(s) and fused ring(s) ((E)-, (Z)-, cis- and trans-forms), isomers due to the presence of asymmetric carbon(s) and the like (R-, S-, α- and, β-forms, enantiomer(s) and diastereomer(s)), optically active substances having optical rotation (D-, L-, d- and l-forms), polar substances by chromatographic separation (more polar and less polar substances), compounds in equilibrium, rotational isomers, a mixture thereof in any proportion and a racemic mixture are included in the present invention. In addition, isomers due to tautomerism are all included in the present invention.

In the present specification, unless otherwise specified, the symbol:

represents that a substituent binds to the back side on the paper surface (in other words, a-configuration), the symbol:

represents that a substituent binds to the front side on the paper surface (in other words, β-configuration), and the symbol:

represents an arbitrary mixture of α-configuration and β-configuration, as would be apparent to those skilled in the art.

[Salts]

The compound represented by general formula (I) can be converted into a salt by a known method.

The salt is preferably a pharmaceutically acceptable salt.

The salt is preferably a water-soluble salt.

Examples of the salt include an acid addition salt, an alkali metal salt, an alkaline earth metal salt, an ammonium salt, an amine salt and the like.

Examples of the acid addition salt include an inorganic acid salt such as a hydrochloride, a hydrobromide, a hydroiodide, a sulfate, a phosphate and a nitrate as well as an organic acid salt such as an acetate, a lactate, a tartrate, a benzoate, a citrate, a methanesulfonate, an ethanesulfonate, a trifluoroacetate, a benzenesulfonate, a toluenesulfonate, an isethionate, a glucuronate and a gluconate.

Examples of the alkali metal salt include a potassium salt, a sodium salt and the like.

Examples of the alkaline earth metal salt include a calcium salt, a magnesium salt and the like.

Examples of the ammonium salt include a tetramethyl ammonium salt and the like.

Examples of the amine salt include a triethylamine salt, a methylamine salt, a dimethylamine salt, a cyclopentylamine salt, a benzylamine salt, phenethylamine salt, a piperidine salt, a monoethanolamine salt, a diethanolamine salt, a tris(hydroxymethyl)aminomethane salt, a lysine salt, an arginine salt, an N-methyl-D-glucamine salt and the like.

In addition, the compound of the present invention can be converted into an N-oxide by an arbitrary method. An N-oxide represents a compound obtained by oxidating a nitrogen atom in the compound represented by general formula (I).

The compound represented by general formula (I) and a salt thereof can be also converted into a solvate.

The solvate is preferably a nontoxic and water-soluble solvate. Examples of the appropriate solvate include a solvate of water and a solvate of an alcohol based solvent (such as a solvate of ethanol). The solvate comprises a solvate of a salt thereof represented by general formula (I).

[Co-Crystals]

The compound represented by the general formula (I) can form a co-crystal with an appropriate co-crystal former. As the co-crystal, pharmaceutically acceptable co-crystal that is formed with a pharmaceutically acceptable co-crystal former is preferable. The co-crystal is typically defined as a crystal that is formed of two or more different molecules by intermolecular interaction that is different from ionic bond. Furthermore, the co-crystal may be a composite of a neutral molecule and a salt. The co-crystal can be prepared by recrystallization from a solvent by a well-known method, for example, melting crystallization, or physically pulverizing the components together. Appropriate co-crystal formers include ones described in WO2006/007448.

[Prodrugs]

A prodrug of the compound represented by general formula (I) refers to a compound which is converted to the compound represented by general formula (I) by a reaction caused by an enzyme, gastric acid and the like in vivo. Examples of the prodrug of the compound represented by general formula (I) include the followings: when the compound represented by general formula (I) has an amino group, a compound obtained by making the amino group in the compound represented by general formula (I) be acylated, alkylated, or phosphorylated (for example, a compound obtained by making an amino group of the compound represented by general formula (I) be eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated and the like); when the compound represented by general formula (I) has a hydroxyl group, a compound obtained by making the hydroxy group in the compound represented by general formula (I) be acylated, alkylated, phosphorylated or borated (for example, a compound obtained by making the hydroxy group in the compound represented by general formula (I) be acetylated, palmitoylated, propanoylated, pivaloylated, succinylated, fumarylated, alanylated, dimethylaminomethylcarbonylated and the like); and when the compound represented by general formula (I) has a carboxy group, a compound obtained by making the carboxy group in the compound represented by general formula (I) be esterified or amidated (for example, a compound obtained by making the carboxy group in the compound represented by general formula (I) be an ethyl ester, a phenyl ester, a carboxymethyl ester, a dimethylaminomethyl ester, a pivaloyloxymethyl ester, a 1-{(ethoxycarbonyl)oxy}ethyl ester, a phthalidyl ester, a (5-methyl-2-oxo-1,3-dioxolen-4-yl)methyl ester, a 1-{[(cyclohexyloxy)carbonyl]oxy}ethyl ester, a methylamide or the like); and the like. These compounds can be prepared by a known method per se. In addition, the prodrug of the compound represented by general formula (I) may be either a hydrate or a non-hydrate. Further, the prodrug of the compound represented by general formula (I) may be a compound which is converted to the compound represented by general formula (I) under a physiological condition as described in "Iyakuhin no kaihatsu (Development of Medicaments)", Vol. 7, "Bunshi sekkei (Molecular Design)", pages 163-198, published by Hirokawa-Shoten Ltd. in 1990.

Furthermore, each atom constituting the compound represented by general formula (I) may also be replaced by an isotope (such as $^2$H, $^3$H, $^{13}$C, $^{14}$C, $^{15}$N, $^{16}$N, $^{17}$O, $^{18}$O, $^{18}$F, $^{35}$S, $^{36}$Cl, $^{77}$Br, and $^{121}$I) and the like.

[Processes for the Preparation of the Compound of the Present Invention]

The compound of the present invention represented by general formula (I) can be prepared by a known method. For example, the compound of the present invention can be prepared by the following method, methods equivalent thereto, or the methods described in Examples. Meanwhile, in each of the following processes for the preparation, a raw material compound may be used as a salt. Examples of the salt used include those described as a pharmaceutically acceptable salt of the compound represented by general formula (I).

The compounds of the present invention represented by general formula (I), for example, can be prepared by a method shown by the following Reaction Scheme.

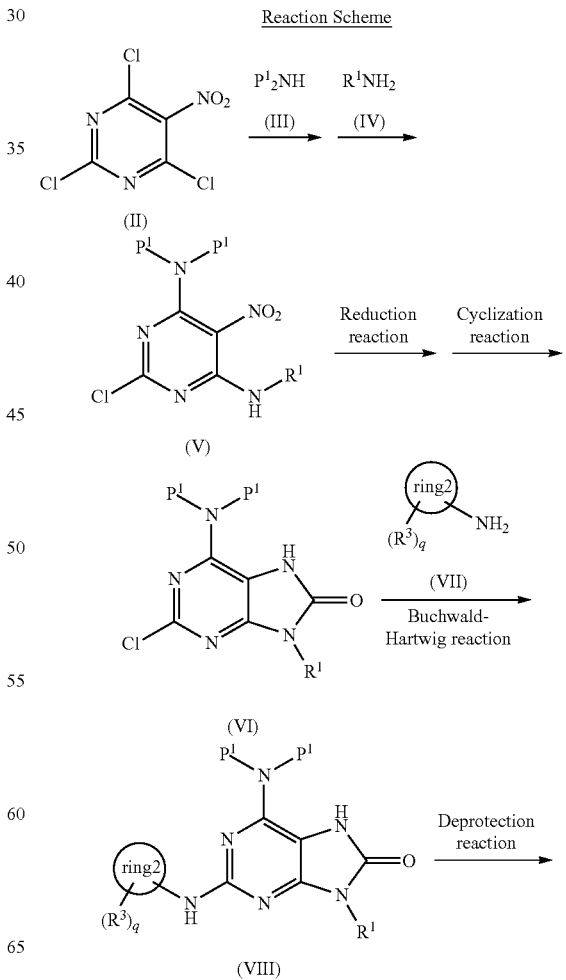

-continued

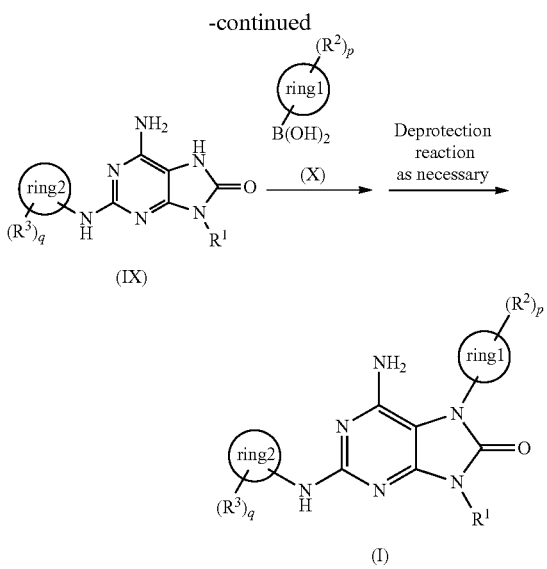

(wherein, $P^1$ represents a benzyl or p-methoxybenzyl group, and the other symbols represent the same meanings as symbols set forth in the above item [1]).

The compound of the present invention having an amino group, a carboxy group, or a hydroxyl group can be prepared as follows. The reactions to Ullman reaction shown in the above-described Reaction Scheme are conducted by using, as necessary, a compound protected by a protecting group which is generally used to these groups, for example, a protecting group described in "Comprehensive Organic Transformations: A Guide to Functional Group Preparations 2nd Edition (Richard C. Larock, John Wiley & Sons Inc, 1999)", and thereafter, a known deprotection reaction, or, for example, a deprotection reaction described in "Comprehensive Organic Transformations: A Guide to Functional Group Preparations 2nd Edition (Richard C. Larock, John Wiley & Sons Inc, 1999)" is conducted.

In Reaction Scheme, a reaction step to prepare the compound represented by general formula (V) from the compound represented by general formula (II) can be performed by the method described in the present specification or a known method.

The compound which is prepared by the reaction represented by general formula (V) is, for example, 2,4,6-trichloro-5-nitropyrimidine(formula (II), CAS No. 4359-87-9) and using amine compound represented by general formula (III), in an organic solvent (such as alcohol-based solvent(such as methanol, ethanol, isopropyl alcohol, butyl alcohol), ether solvent (such as diethyl ether, tetrahydrofuran, diethylene glycol dimethyl ether, dioxane, dimethoxyethane), halide solvent (such as methylene chloride, chloroform), dimethylformamide, dimethylsulfoxide, or a solvent obtained by appropriately mixing these organic solvents) or in mixed solvents of these organic solvent and water, in the presence or absence of a base (such as triethylamine, diisopropylethylamine), a compound prepared by reacting at about −20° C. to 180° C., and using amine compound represented by general formula (IV), organic solvent (such as alcohol-based solvent(such as methanol, ethanol, isopropyl alcohol, butyl alcohol), ether solvent (such as diethyl ether, tetrahydrofuran, diethylene glycol dimethyl ether, dioxane, dimethoxyethane), halide solvent (such as methylene chloride, chloroform), dimethylformamide, dimethylsulfoxide, or a solvent obtained by appropriately mixing these organic solvents) or in mixed solvents of these organic solvent and water, in the presence or absence of a base (such as triethylamine, diisopropylethylamine), is prepared by reacting at about −20° C. to 180° C.

In Reaction Scheme, a reaction step to prepare the compound represented by general formula (VI) from the compound represented by general formula (V) can be performed by the method described in the present specification or a known method. The compound which is prepared by the reaction represented by general formula (VI) is, for example, using the compound represented by general formula (V), in an organic solvent (such as acetate, ethanol, methanol, dimethylformamide, toluene, or a solvent obtained by appropriately mixing these organic solvents) or in mixed solvents of these organic solvent and water, in the presence of a catalyst (such as an iron catalyst (such as iron, iron chloride, iron-ammonium chloride), a zinc catalyst (such as zinc, zinc-ammonium chloride), a nickel catalyst (such as nickel chloride), an indium catalyst (such as indium), tin catalyst (such as tin, tin chloride), or a catalyst obtained by appropriately mixing these catalyst), a compound (5-aminopyrimidine derivative) prepared by reacting at room temperature to about 80° C., or under a hydrogen atmosphere, in organic solvent (such as methanol, ethanol, ethyl acetate, tetrahydrofuran, acetate, 1,2-dimethoxyethane or a solvent obtained by appropriately mixing these organic solvents) or in mixed solvents of these organic solvent and water, in the presence of a catalyst (such as a silver catalyst (such as silver acetate), platinum catalyst(such as platinum-carbon, platinum oxide), rhodium catalyst (such as rhodium-carbon), iron catalyst (such as iron acetate), ruthenium catalyst (such as ruthenium-carbon), palladium catalyst (such as palladium-carbon), zinc catalyst (such as zinc bromide, zinc iodide, zinc acetate), raney nickel, or a catalyst obtained by appropriately mixing these catalyst), a compound (5-aminopyrimidine derivative) prepared by reacting at room temperature to about 80° C., and using a Carbonyl compound derivative(such as phosgene, triphosgene, carbonyl diimidazole, carbonyl dipyrrole, urea, dimethyl carbonate, diethyl carbonate), in an organic solvent (such as toluene, methylene chloride, tetrahydrofuran, chlorobenzene, or a solvent obtained by appropriately mixing these organic solvents), in the presence or absence of an acid (such as hydrochloric acid, acetic acid) or a base (such as triethylamine, pyridine, sodium methoxide), is prepared by reacting at about −20° C. to 150° C.

In Reaction Schemes, a reaction step (Buchwald-Hartwig reaction) to prepare the compound represented by general formula (VIII) from the compound represented by general formula (VI) can be performed by the method described in the present specification or a known method. The compound which is prepared by the reaction represented by general formula (VIII) is, for example, using the compound represented by general formula (VI) and general formula (VII), in an organic solvent (such as dioxane, toluene, dimethylformamide, N-methylpyrrolidone, or a solvent obtained by appropriately mixing these organic solvents), in the presence of a palladium catalyst (such as palladium acetate, allylpalladium(II) chloride dimer($Pd_2Cl_2$ (allyl)$_2$), and tris(dibenzylideneacetone)dipalladium(0) ($Pd_2$ (dba)$_3$)), and in the presence of a phosphorus catalyst(such as triphenylphosphine, tributylphosphine, tricyclohexylphosphine), in the presence of a base (such as cesium carbonate, sodium butoxide, tripotassium phosphate), is prepared by reacting at room temperature to about 180° C.

In Reaction Schemes, a reaction step (a deprotection reaction of a protecting group of an amino group reaction)

to prepare the compound represented by general formula (IX) from the compound represented by general formula (VIII) can be performed by the method described in the present specification or a known method, for example, can be performed by the method described in the Protective Groups in Organic Synthesis (T. W. Greene, John Wiley & Sons Inc. (1999)).

The compound represented by general formula (IX) which is prepared by the reaction is, for example, using the compound represented by general formula (VIII), prepared by a deprotection reaction under an acidic condition or a deprotection reaction by hydrogenolysis. Specifically, a deprotection reaction under an acidic condition (such as a deprotection reactions of tert-butoxycarbonyl group, trityl group, p-methoxybenzyl group) is, for example, in a water or an organic solvent (such as methylene chloride, chloroform, dioxane, ethyl acetate, anisole), an organic acid (such as acetic acid, trifluoroacetic acid, methanesulfonic acid), or an inorganic acid (such as hydrochloric acid, sulfuric acid) or in these miture (such as hydrogen bromide/acetic acid), is prepared by reacting at about 0° C. to 180° C. On the other hand, a deprotection reaction by hydrogenolysis (such as a deprotection reactions such as benzyl group, benzhydryl group, benzyloxycarbonyl group, allyloxycarbonyl group) is, for example, organic solvent (such as ether solvent (such as tetrahydrofuran, dioxane, dimethoxyethane, diethyl ether), alcohol-based solvent(such as methanol, ethanol), benzene type solvents (such as benzene, toluene), ketone type solvents (such as acetone, methyl ethyl ketone), nitrile solvents (such as acetonitrile), amide solvents (such as dimethylformamide), in water, ethyl acetate, acetic acid, or a mixed solvent of two or more thereof), in the presense of catalyst (such as palladium-carbon, palladium black, palladium hydroxide, platinum oxide, Raney nickel), in a hydrogen atmosphere under normal pressure or under pressurization or in the presence of ammonium formate, is carried out at about 0° C. to 200° C.

In Reaction Schemes, a reaction step (Ullman reaction) to prepare the compound represented by general formula (I) from the compound represented by general formula (IX) can be performed by the method described in the present specification or a known method. The compound represented by general formula (I) which is prepared by the reaction is, for example, using the compound represented by general formula (IX) and general formula (X), in a solvent (such as acetone, methanol, propanol, acetonitrile, methylene chloride, toluene, dichloroethane, dimethylformamide, dimethylsulfoxide, or a solvent obtained by appropriately mixing these organic solvents) or in mixed solvents of these organic solvent and water, in the presence of a copper catalyst (such as copper oxide, copper acetate, copper chloride, copper bromide, copper iodide, copper nitrate), in the presence of a base (such as triethylamine, potassium carbonate, sodium carbonate, potassium butoxide, pyridine, dimethylaminopyridine, sodium bis (trimethylsilyl) amide, sodium acetate, diazabicycloundecene (DBU), diisopropylethylamine, tetramethylethylenediamine), is prepared by reacting at room temperature to about 150° C. Incidentally, there is a compound represented by the general formula (I) which is produced by carrying out deprotection reaction as necessary after this Ullmann reaction.

The deprotection reaction can be carried out by the method described in the present specification or a known method, for example, the Protective Groups in Organic Synthesis (T. W. Greene, John Wiley & Sons Inc. (1999)).

Examples of the deprotection reaction include, specifically, (1) deprotection reaction by alkaline hydrolysis, (2) deprotection reaction under acidic conditions, (3) deprotection reaction by hydrogenolysis, (4) deprotection reaction using metal complex, (5) deprotection reaction using metal, (6) deprotection of silyl group reaction and the like.

Explaining each of these methods specifically, deprotection reaction by alkaline hydrolysis (such as deprotection reaction of trifluoroacetyl group) is performed, for example, in the organic solvent (such as methanol, tetrahydrofuran, dioxane), using alkali metal hydroxides (such as sodium hydroxide, potassium hydroxide, lithium hydroxide), alkaline earth metal hydroxides (such as barium hydroxide, calcium hydroxide) or carbonates (such as sodium carbonate, potassium carbonate) or an aqueous solution thereof, or a mixture thereof, at about 0° C. to 40° C. Deprotection reaction under acid conditions (such as deprotection reaction of butoxycarbonyl group, trityl group), for example, in water or an organic solvent (such as methylene chloride, chloroform, dioxane, ethyl acetate, anisole), in an organic acid (such as acetic acid, trifluoroacetic acid, methanesulfonic acid) or an inorganic acid (such as hydrochloric acid, sulfuric acid) or a mixture thereof (such as hydrogen bromide/acetic acid) is carried out at about 0° C. to 100° C. Deprotection reaction by hydrogenolysis (such as deprotection reaction of benzyl group, benzhydryl group, benzyloxycarbonyl group, allyloxycarbonyl group) is performed, for example, in an organic solvent (such as an ether solvent (such as tetrahydrofuran, dioxane, dimethoxyethane, diethyl ether), an alcoholic solvent (such as methanol, ethanol), a benzene solvent (such as benzene, toluene), a ketone-based solvent (such as acetone, methyl ethyl ketone), a nitrile-based solvent (such as acetonitrile), an amide type solvent (such as dimethylformamide), water, ethyl acetate, acetic acid or a mixed solvent of two or more thereof, in the presence of a catalyst (such as palladium-carbon, palladium black, palladium hydroxide, platinum oxide, Raney nickel), in a hydrogen atmosphere under normal pressure or under pressurization or in the presence of ammonium formate, at a temperature of about 0° C. to 200° C. Deprotection reaction using a metal complex (such as deprotection reaction such as allyloxycarbonyl group), is performed, for example, in an organic solvent (such as dichloromethane, dimethylformamide, tetrahydrofuran, ethyl acetate, acetonitrile, dioxane, ethanol), water or a mixed solvent thereof, in the presence of a trap reagent (such as tributyltin hydride, triethylsilane, dimedone, morpholine, diethylamine, pyrrolidine), an organic acid (such as acetic acid, formic acid, 2-ethylhexanoic acid) and/or an organic acid salt (such as sodium 2-ethylhexanoate, potassium 2-ethylhexanoate), in the presence or absence of a phosphine-based reagent (such as triphenylphosphine), using a metal complex (such as tetrakistriphenylphosphine palladium (0), bis (triphenylphosphine) palladium (II) dichloride, palladium (II) acetate, chlorotris (triphenylphosphine) rhodium (I)), at about 0° C. to 40° C. Deprotection reactions using metals is performed, for example, in an acidic solvent (such as acetic acid, a buffer solution of pH 4.2 to 7.2 or a mixture solution thereof with an organic solvent such as tetrahydrofuran), in the presence of powdered zinc, while applying ultrasonic waves if necessary, at about 0° C. to 40° C. The deprotection reaction of the silyl group is performed, for example, in an organic solvent miscible with water (such as tetrahydrofuran, acetonitrile), using tetrabutylammonium fluoride, at about 0° C. to 40° C. If necessary, the reaction may be followed by conversion to the desired salt by a known method subsequent to this reaction.

In Reaction Schemes, the compounds represented by general formula (III), general formula (IV), general formula (VII), and general formula (X), used as the starting materials are known or can be easily prepared by using a known method, for example, a method described in "Comprehensive Organic Transformations: A Guide to Functional Group Preparations 2nd Edition (Richard C. Larock, John Wiley & Sons Inc, 1999)".

Among the compounds of the present invention represented by general formula (I), compounds other than those compounds described above can be prepared by combining the methods described in Examples in the present specification or a known method, for example, a method described in "Comprehensive Organic Transformations: A Guide to Functional Group Preparations 2nd Edition (Richard C. Larock, John Wiley & Sons Inc, 1999)".

In the present specification, a reaction which involves heating in each of the reactions can be performed by using a water bath, an oil bath, a sand bath or a microwave as apparent to those skilled in the art.

In the present specification, a solid phase-supported reagent which is supported by a macromolecular polymer (such as polystyrene, polyacrylamide, polypropylene and polyethylene glycol) may be used appropriately, in each of the reactions.

In the present specification, the reaction product in each of the reactions can be purified by a conventional purification means. Examples of the purification means include distillation under a normal pressure or a reduced pressure, high performance liquid chromatography which uses silica gel or magnesium silicate, thin-layer chromatography, an ion exchange resin, a scavenger resin, column chromatography, or methods such as washing, recrystallization and the like. The purification may be performed at each of reactions or may be performed after the completion of several reactions.

[Toxicity]

The toxicity of the compound of the present invention is low, and therefore, the compound of the present invention can be used as a medicine safely.

[Application to Pharmaceuticals]

The compound of the present invention has a Brk inhibitory activity, and therefore, the compound of the present invention is useful as an agent for treating Brk-related diseases, for example, cancer and the like.

More specific examples of cancer include breast cancer, ovarian cancer, large bowel cancer (such as, colon cancer), lung cancer (such as non-small-cell lung cancer), prostate cancer, head and neck cancer (such as oral squamous cell cancer, head and neck squamous cell cancer, pharyngeal cancer, laryngeal cancer, tongue cancer, thyroid cancer, and acoustic schwannoma), lymphoma (such as B-cell lymphoma, and T-cell lymphoma), brain tumor, glioma, pituitary adenoma, uveal malignant melanoma, meningioma, thymoma, mesothelioma, esophageal cancer, gastric cancer, duodenal cancer, hepatocellular cancer, bile duct cancer, gallbladder cancer, pancreatic cancer, renal cell cancer, renal pelvis-ureteral cancer, bladder cancer, penile cancer, testicular cancer, uterine cancer, vaginal cancer, vulvar cancer, skin cancer (such as malignant melanoma (melanoma)), malignant bone tumor, soft tissue sarcoma, chondrosarcoma, leukemia (such as acute myeloid leukemia, acute lymphocytic leukemia, chronic myeloid leukemia, and chronic lymphocytic leukemia), myelodysplastic syndrome, multiple myeloma and the like.

In the present invention, the treatment of cancer includes causing at least one of reduction in tumor size, the suppression (delay or stop) of tumor growth, the suppression (delay or stop) of tumor metastasis, the suppression (prevention or delay) of recurrence, and the alleviation of one or more symptoms associated with cancer.

The compound of the present invention may be administered as a combined agent by being combined with other drug(s) for the purpose of:
1) complementation and/or enhancement of the preventing and/or treating effect of the compound,
2) improvement in kinetics·absorption, and reduction of the dose of the compound, and/or
3) reduction of the side effect of the compound.

The combined agent of the compound of the present invention with other drug(s) may be administered in the form of a compounding agent in which both ingredients are compounded in a preparation or may be administered by means of separate preparations. The case of being administered by means of separate preparations includes concomitant administration and administrations with a time difference. In addition, in the case of the administrations with a time difference, the compound of the present invention may be firstly administered, followed by administration of the other drug(s). Alternatively, the other drug(s) may be firstly administered, followed by administration of the compound of the present invention. A method for administering the compound of the present invention and that for administering the other drug(s) may be the same or different.

The disease against which the above-described combined agent exhibits the preventing and/or treating effect is not particularly limited as long as the disease is that against which the preventing and/or treating effect of the compound of the present invention is complemented and/or enhanced.

Examples of the other drug(s) for complementation and/or enhancement of the treating effect of the compound of the present invention on cancer include anticancer drugs which are an alkylating agent, an antimetabolite, an anticancer antibiotic, a plant-derived preparation, a hormone preparation, a platinum compound, a immunomodulator, a topoisomerase inhibitor, a biological response modifier, a kinase inhibitor, an immune checkpoint inhibitor, a histone deacetylase (HDAC) inhibitors, a proteasome inhibitors, an anti-CD20 antibody, an anti-HER2 antibody, an anti-EGFR antibody, an anti-VEGF antibody and the like.

Examples of the alkylating agent include cyclophosphamide, ifosfamide, dacarbazine, nimustine hydrochloride, ranimustine, bendamustine, thiotepa, carboquone and the like.

Examples of the antimetabolite include methotrexate, pemetrexed, fluorouracil, tegafur, tegafur/uracil, tegafur/gimestat/potassium otastat, doxifluridine, capecitabine, cytarabine, gemcitabine hydrochloride, fludarabine, nelarabine, carmofur, procarbazine hydrochloride and the like.

Examples of the anticancer antibiotic include mitomycin C, doxorubicin hydrochloride, aclarubicin hydrochloride, pirarubicin hydrochloride, epirubicin, chromomycin A3, bleomycin, peplomycin sulfate, therarubicin and the like.

Examples of the plant-derived preparation include irinotecan hydrochloride, etoposide, vincristine sulfate, vinblastine sulfate, vindesine sulfate, vinorelbine ditartrate, docetaxel hydrate, eribulin mesylate, paclitaxel and the like.

Examples of the hormone preparation include estramustine phosphate sodium, flutamide, bicalutamide, goscrelin acetate, leuprorelin acetate, tamoxifen citrate, toremifene citrate, anastrozole, letrozole, exemestane, mepitiostane, medroxyprogesterone acetate, epitiostanol, fosfestrol, fadrozole hydrochloride hydrate, abiraterone, fulvestrant, aminoglutethimide and the like.

Examples of the platinum compound include carboplatin, cisplatin, nedaplatin, oxaliplatin and the like.

Examples of the immunomodulator include lenalidomide and the like.

Examples of the topoisomerase inhibitor include topotecan, sobuzoxane and the like.

Examples of the biological response modifier include interferon γ-1a, teceleukin and the like.

Examples of the kinase inhibitor include an EGFR inhibitor including erlotinib, gefitinib, afatinib, and neratinib, a MEK inhibitor including tramethinib, a PI3K inhibitor including idelarisib, a JAK inhibitor including luxolitinib, and tofacitinib, a CDK inhibitor including parvociclib, an HER2 inhibitor including lapatinib, a BCR-ABL inhibitor including imatinib, nilotinib, and bostinib, mTOR inhibitors including everolimus, temsirolimus, and rapamycin, an ALK inhibitor including crizotinib, a multikinase inhibitor including regorafenib, sorafenib, sunitinib, and dasatinib and the like.

Examples of the immune checkpoint inhibitor include an anti-CTLA-4 antibody including ipilimumab, tremelimumab, and AGEN-1884, an anti-PD-1 antibody including nivolumab, pembrolizumab, REGN-2810, PDR-001, BGB-A317, AMP-514(MEDI0680), BCD-100, IBI-308, JS-001, PF-06801591, and TSR-042, an anti-PD-L1 antibody including Atezolizumab (RG7446/MPDL3280A), Avermab (MSB0010718C), Durubarumab (MEDI 4736), BMS-936559, CA-170, and LY-3300054, an anti-PD-L2 antibody including rHIgM12B7, PD-L1 fusion protein and PD-L2 fusion protein including AMP-224, an anti-Tim-3 antibody including MBG 453, an anti-LAG-3 antibody including BMS-986016, and LAG 525, an anti-KIR antibody including Lirilumab and the like.

Examples of the Histone deacetylase (HDAC) inhibitors include vorinostat, panovinostat and the like.

Examples of the Proteasome inhibitor include bortezomib and the like.

Examples of the anti-CD20 antibody include rituximab, ibritumomab, ibritumomab tiuxetan, ocrelizumab and the like.

Examples of the anti-HER2 antibody include trastuzumab, trastuzumab emtansine, pertuzumab and the like.

Examples of the anti-EGFR antibody include cetuximab, panitumumab and the like.

Examples of the anti-VEGF antibody include bevacizumab and the like.

A mass ratio of the compound of the present invention and other drug(s) is not particularly limited.

Arbitrary two or more kinds of other drugs may be administered in combination.

In addition, other drug(s) for complementation and/or enhancement of the preventing and/or treating effect of the compound of the present invention includes not only that which has been found up to now but also that which will be found in future based on the above-described mechanism.

In order to use the compound of the present invention as a single agent or as a combined agent which combines the compound of the present invention with other drug(s) for the purpose of the prevention and/or treatment of the above-described disease, the substance which is an active ingredient is normally formulated with various types of pharmaceutically acceptable carriers such as additives and solvents and is administered systemically or locally in the form of an oral preparation or a parenteral preparation. Here, a pharmaceutically acceptable carrier means a substance other than an active ingredient which is generally used for formulation of a medicine. It is preferable that the pharmaceutically acceptable carrier does not exhibit a pharmacological action in a dose of the formulation, is harmless, and does not interfere with a therapeutic effect of the active ingredient. In addition, the pharmaceutically acceptable carrier may also be used for the purpose of enhancing utility of the active ingredient and the formulation, making formulation easy, stabilizing quality, improving usability or the like. Specifically, a substance described in "Iyakuhin tenkabutsu jiten (Japanese Pharmaceutical Excipients Directory)" (edited by Japan pharmaceutical Excipients Council), YAKUJI NIPPO LIMITED published in 2000 or the like may be selected appropriately according to a purpose.

Dosage forms for administration includes, for example, oral preparation (e.g.: tablets, capsules, granules, powders, oral solutions, syrups, oral jelly agents, etc.), oro-mucosal preparation (e.g.: tablets for oro-mucosal application, sprays for oro-mucosal application, semi-solid preparations for oro-mucosal application, gargles, etc.), preparations for injection (e.g.: injections, etc.), preparations for dialysis (e.g.: dialysis agents, etc.), preparation for inhalation (e.g.: inhalations, etc.), preparation for ophthalmic application (e.g.: ophthalmic liquids and solutions, ophthalmic ointments, etc.), preparation for otic application (e.g.: ear preparation, etc.), preparations for nasal application (nasal preparations, etc.), preparation for recta (e.g.: suppositories, semi-solid preparations for rectal application, enemas for rectal application, etc.), preparations for vaginal application (e.g.: tablets for vaginal use, suppositories for vaginal use, etc.) and preparation for cutaneous application (e.g.: solid preparations for cutaneous application, liquids and solutions for cutaneous application, sprays, ointment, creams, gels, patches, etc.).

[Oral Preparation]

Oral preparation include, for example, tablets, capsules, granules, powders, liquids and solution for oral administration, syrups, Jellies for oral administration, etc. As oral preparation, there are Immediate-release dosage forms showing a release pattern of active substances that is not intentionally modified and modified-release dosage forms are preparations showing modified pattern of active substances that is suitably modified for the desired purpose by means of a specific formulation design and/or manufacturing methods. Modified-release dosage forms include enteric-coated and extended-release preparations. Enteric-coated (delayed-release) preparations release the bulk of the active substances not in stomach but mainly in small intestine, in order to prevent degradation or decomposition of the active substances in stomach or to decrease the irritation of the active substances on stomach. Enteric-coated preparations are generally coated with an acid-insoluble enteric film. Extended-release preparations are designed to control the release rate and release period of active substances and to restrict the release to appropriate sites in the gastrointestinal tracts in order to decrease the dosing frequency and/or to reduce adverse or side effects. Extended-release preparations are generally prepared by using suitable agents that prolong the release of the active substances. Oral dosage forms such as capsules, granules and tablets can be coated with appropriate coating agents, such as sugars, sugar alcohols, or polymers, for the purpose of enabling the ingestion easy or of preventing degradation of the active substances.

(1) Tablets

Tablets are solid preparation having a desired shape and size, intended for oral administration, and include orally disintegrating tablets, chewable tablets, effervescent tablets, dispersible tablets, soluble tablets besides generally called tablets such as plain tablets, film-coated tablets, sugar-coated tablets, multi-layered tablets and pressure-coated tablets, etc. Plain tables are usually prepared according to the following methods (a), (b) and (c):

(a) Mix homogeneously active substances and excipients such as diluents, binders and disintegrators, granulate with water or a binder solution by suitable methods, mix with a lubricant, and then compress into a desired shape and size;

(b) Mix homogeneously active substances and excipients such as diluents, binders, and disintegrators, and then directly compress, or compress after adding active substances and lubricant to granules previously prepared from excipients and then mixing homogeneously, (c) Mix homogeneously active substances and excipients such as diluents and binders, moisten with a solvent, form into a certain shape and size, and then dry by suitable methods; Film-coated tablets can be prepared, usually, by coating plain tablets using suitable coating agents such as polymers. Sugar-coated tablets can be prepared, usually, by coating plain tablets using suitable coating agents including sugars and sugar alcohols. Multiple-layer tablets can be prepared by compressing granules of different compositions to form layered tablets by a suitable method. Pressure-coated tablets can be prepared by compressing granules to cover inner core tablets with different compositions. In addition, tablets can be prepared as enteric coated tablets or timed-release tablet by suitable well-known methods. Orally disintegrating tablets, chewable tablets, effervescent tablets, dispersible tablets, soluble tablets are tablets which are added distinct role by selecting suitable excipients, and can be prepared according to said methods. Orally disintegrating tablets are tablets which are quickly dissolved or disintegrated in the oral cavity; Chewable tablets are tablets which are administered by chewing; Effervescent tablets are tablets which are quickly dissolved or dispersed with bubbles in water; Dispersible tablets are tablets which are administered after having been dispersed in water, Soluble tablets are tablets which are administered after having been dissolved in water. Effervescent tablets can be prepared using suitable acidic substances and carbonates or hydrogen carbonates as excipients.

(2) Capsules

Capsules are preparations enclosed in capsules or wrapped with capsule bases, intended for oral administration. Capsules are classified into hard capsules and soft capsules. Hard capsules can be prepared by a method where a homogeneous mixture of active substances with diluents and other suitable excipients, or granules or formed masses prepared by suitable methods, are filled into capsule shells as they are or after slight compression. Soft capsules can be prepared by a method where active substances and suitable excipients are mixed, enclosed by a suitable capsule base such as gelatin plasticized by addition of glycerin, D-sorbitol, etc. and molded in a suitable shape and size. Capsules can be prepared as enteric-coated or extended-release capsules by a suitable well-known method. Coloring agents and preservatives, etc. may be added to the capsule bases.

(3) Granules

Granules are preparations prepared by granulation, and include effervescent granules besides generally called granules. Granules can be prepared by the following methods (a), (b), and (c);

(a) To powdery active substances add diluents, binders, disintegrators, or other suitable excipients, mix to homogenize, and granulate by a suitable method;

(b) To previously granulated active substances add excipients such as diluents, and mix to homogenize;

(c) To previously granulated active substances add excipients such as diluents, and granulate by a suitable method;

Granules can be coated if necessary, and can be prepared as enteric-coated or extended-release granules. Effervescent granules can be prepared using suitable acidic substances and carbonates or hydrogen carbonates. Effervescent granules are granules which are quickly dissolved or dispersed with bubbles in water. Granules can be prepared as fine grain agents by adjusting particle size.

(4) Powders

Powders are preparations in powder form, and are usually prepared by homogeneously mixing active substances with diluents or other suitable excipients.

(5) Liquids and Solution for Oral Administration

Liquids and solution for oral administration are preparations in liquid form or flowable and viscous gelatinous state, and elixirs, suspensions, emulsions and lemonades are included in this category besides generally called Liquids and solution for oral administration. Liquids and solution for oral administration are usually prepared by dissolving, emulsifying or suspending active substances in purified water together with excipients, and by filtering if necessary. Elixirs are clear, sweetened and aromatic liquid preparations, containing ethanol, and are usually prepared by dissolving solid active substances or their extractives in ethanol and purified water, adding aromatic agents and sucrose, other sugars or sweetening agents, and clarifying by filtration or other procedure. Suspensions are liquid preparations of active substances suspended finely and homogeneously in a vehicle, and are usually prepared by adding suspending agent or other suitable excipients and purified water or oil to solid active substances, and suspending homogeneously as the whole by a suitable method. Emulsions are liquid preparations of active substances emulsified finely and homogeneously in a liquid vehicle, and are usually prepared by adding emulsifying agents and purified water to liquid active substances, and emulsifying finely and homogeneously by a suitable method. In addition, Lemonades are sweet and sour, clear liquid preparations, intended for oral administration.

(6) Syrups

Syrups are viscous liquid or solid preparations containing sugars or sweetening agents, and include preparation for syrups. Syrups are usually prepared by dissolving, mixing, suspending or emulsifying active substances in a solution of sucrose, other sugars or sweetening agents, or in simple syrup. Where necessary, the mixture is boiled, and filtered while hot.

Preparations for syrups are preparations in form of granules or powders, which becomes syrups by adding water. They may be termed "dry syrups". Preparations for syrups are usually prepared with sugars or sweetening agents according to said preparation method of granules or powders.

(7) Jellies for Oral Administration

Jellies for oral administration are non-flowable gelatinous preparations having a certain shape and size, and usually prepared by mixing active substances with suitable excipients and polymer gel base, gelatinizing and forming into a certain shape and size by a suitable method.

[Preparation for Oro-Mucosal Application]

(1) Tablets for Oro-Mucosal Application

Tablets for oro-mucosal application are solid preparations having a certain form, and include troches/lozenges, sublingual tablets, buccal tablets, mucoadhesive tablets and medicated chewing gums. Preparations for oro-mucosal application are usually prepared according to said method of tablets. Troches/lozenges are tablets for oro-mucosal application, which are gradually dissolved or disintegrated in the mouth;

Sublingual tablets are tablets for oro-mucosal application, from which active substances are quickly dissolved sublingually and absorbed via the oral mucosa; Buccal tablets are tablets for oro-mucosal applications, from which the active substances are dissolved gradually between the cheek and teeth, and absorbed via the oral mucosa; Mucoadhesive tablets are tablets for oro-mucosal application that are applied by adhesion to the oral mucosa; Medicated chewing gums are tablets for oro-mucosal application, releasing active substances by chewing.

(2) Spray for Oro-Mucosal Application

Spray for oro-mucosal application are preparation that are applied active substances by spraying into the oral cavity in mist, powder, foam or paste forms, and are usually prepared by dissolving or suspending active substances and suitable excipients in a solvent, filter, where necessary, and fill into a container together with liquefied or compressed gas, or dissolving or suspending active substances and suitable excipients in a solvent, and fill into a container, and fit with a pump for spraying.

(3) Semi-Solid Preparations for Oro-Mucosal Application

Semi-solid preparations for oro-mucosal application are preparation in cream, gel or ointment forms, intended for application to the oral mucosa. Semi-solid preparations for oro-mucosal application are usually prepared by emulsifying active substances together with excipients using purified water and oil component such as petrolatum, or by homogenizing active substances together with suitable excipients using polymer gel or oil and fats as the base. Creams are semi-solid preparations, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. These components have the following constituents. Oil-phase component: Vaseline, fatty alcohols, etc., with or without emulsifying agents or other suitable excipients. Water-phase component: purified water with or without emulsifying agents or other suitable excipients. Gels are gelatinous preparations. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing. Ointments are semi-solid preparations, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and kneading the whole to make homogeneous. Hydrophilic ointments are usually prepared by warming to melt hydrophilic bases such as macrogol, adding and mixing active substances in the bases, and kneading the whole to make homogenous.

(4) Preparations for Gargle

Preparations for gargle are liquid preparations intended to apply locally to the oral and throat cavities. Solid type preparations to be dissolved in water before use are also included in this category. Preparations for gargle are usually prepared by dissolving active substances in a solvent together with suitable excipients, and filtering where necessary. Solid preparations are prepared according to said method of tablets or granules.

[Preparation for Injection]

(1) Injections

Injections are sterile preparations to be administered directly into the body through skin, muscle or blood vessel, usually in form of a solution, a suspension or an emulsion of active substances, or of a solid that contains active substances to be dissolved or suspended before use, and include freeze-dried injections, powders, prefilled syringes, cartridges, parenteral infusions, implants/pellets and prolonged-release injections besides generally called injections. Injections are prepared by the following method (a) and (b):

(a) Dissolve, suspend or emulsify active substances with or without excipients in water for injection or an aqueous or non-aqueous vehicle homogeneously, fill into containers for injection, seal, and sterilize.

(b) Dissolve, suspend or emulsify active substances with or without excipients in water for injection or an aqueous or non-aqueous vehicle, and filtrate aseptically, or prepare aseptically a homogeneous liquid, fill into containers for injection, and seal;

Freeze-dried injections are usually prepared by dissolving active substances with or without excipients such as diluents in water for injection, sterilizing the solution by aseptic filtration, filling the filtrate directly into individual containers for injection and being freez-dried, or dividing the filtrate in special containers, being freeze-dried and transferred into individual containers for injection. Powder for injections are usually prepared by filtrating aseptically a solution of active substances, obtaining powders by crystallization from the solution or mixing additionally the powders with sterilized excipients, and filling the powders into individual containers for injections. Prefilled syringes for injections are usually prepared by dissolving, suspending or emulsifying active substances with or without excipients in a vehicle, and filling into syringes. Cartridges are used by fixing in an injection device for exclusive use. Cartridges for injection are usually prepared by dissolving, suspending or emulsifying active substances with or without excipients in a vehicle, and filling into cartridges. Parenteral infusions are usually injections of not less than 100 mL, intended for intravenous administration. Implants/Pellets are solid or gel-like form injections, intended for subcutaneous or intramuscular administration by means of an implant device or operative treatment, for the purpose of releasing active substances for a long period of time. Implants/Pellets are usually prepared in a form of pellet, microsphere or gel using biodegradable polymers. Prolonged release injections are injections to be used for intramuscular administration, for the purpose of releasing active substances for a long period of time, and usually prepared by dissolving or suspending active substances in a non-aqueous vehicle such as vegetable oil, or by suspending microspheres prepared with biodegradable polymers.

[Preparations for Dialysis]

(1) Dialysis Agents

Dialysis agents are preparations in liquid, or in solid which are to be dissolved before use, intended for peritoneal dialysis or hemodialysis, and include peritoneal dialysis agents and hemodialysis agents. Peritoneal dialysis agents are sterile dialysis agents, intended to be used for peritoneal dialysis, and are usually prepared by dissolving active substances with suitable excipients in a vehicle to make a certain volume, or by filling active substances combined with suitable excipients in a container, and sealing it. Sterilize if necessary. In the case of solid preparations to be dissolved before use, it can be prepared according to said preparation method of tablets or granules. Hemodialysis agents are dialysis agents to be used for hemodialysis, and are usually prepared by dissolving active substances with excipients in a vehicle to make a certain volume, or by filling active substances with excipients in a container. In the case of the solid preparations to be dissolved before use, it can be prepared according to said preparation method of tablets or granules.

[Preparation for Inhalation]

(1) Inhalations

Inhalations are preparations intended for administration as aerosols to the bronchial tubes or lung. Inhalations are classified to dry powder inhalers, inhalation liquid preparations and metered-dose inhalers. Dry powder inhalers are preparations which deliver a constant respiratory intake, intended for administration as solid particle aerosols, and are usually prepared by pulverizing active substances into fine particles. Where necessary, lactose or other suitable excipients are added to make homogeneous mixture. Inhalation liquid preparations are liquid inhalations which are administered by an inhalation device such as operating nebulizer. Inhalation liquid preparations are usually prepared by mixing active substances with a vehicle and suitable isotonic agents and/or pH adjusting agents to make a solution or suspension, and by filtering where necessary. Metered-dose inhalers are preparations which deliver a constant dose of active substances from the container together with propellant filled in. Metered-dose inhalers are usually prepared by dissolving active substances with a suitable dispersing agents and stabilizers in a vehicle to make a solution or suspension, and by filling in pressure-resistant containers together with liquid propellant, and setting metering valves.

[Preparation for Ophthalmic Application]

(1) Ophthalmic Liquids and Solutions

Ophthalmic liquids and solutions are sterile preparations of liquid, or solid to be dissolved or suspended before use, intended for application to the conjunctival sac or other ocular tissues. Ophthalmic liquids and solutions are usually prepared by dissolving, suspending active substances in a vehicle after adding excipients to make a constant volume, or mixing active substances and excipients, and filling into containers.

(2) Ophthalmic Ointments

Ophthalmic ointments are sterile preparations of semi-solid, intended for application to the conjunstival sac and other ocular tissues. Ophthalmic ointments are usually prepared by mixing homogeneously solution of or finely powdered active substances with petrolatum or other bases, and filling into containers.

[Preparation for Otic Application]

(1) Ear Preparation

Ear preparations are liquid, semi-solid, or solid preparations which are to be dissolved or suspended before use, intended for application to the external or internal ear. Ear preparations are usually prepared by filling in containers with liquids in which active substances and excipients are dissolved or suspended in a vehicle to make a constant volume, or with powders in which active substances and excipients are mixed.

[Preparations for Nasal Application]

(1) Nasal Preparations

Nasal preparations are preparations intended for application to the nasal cavities or nasal mucous membrane. Nasal preparations are classified into Nasal dry powder inhalers and Nasal liquid preparations. Nasal dry powder inhalers are fine powdered preparations, intended for application to the nasal cavities. Nasal dry powder inhalers are usually prepared by pulverizing active substances into moderately fine particles, or by mixing homogeneously with excipients where necessary. Nasal liquids and solutions are liquid preparations, or solid preparations to be dissolved or suspended before use, intended for application to the nasal cavities. Nasal liquids and solutions are usually prepared by dissolving or suspending active substances in a vehicle together with excipients, and filtering where necessary. Isotonic agents and/or pH adjusting agents may be used.

[Preparations for Rectal Application]

(1) Suppositories for Rectal Application

Suppositories for rectal application are semi-solid preparations of a desired shape and size, intended for intrarectal application, which release active substances by melting at body temperature or dissolving or dispersing gradually in the secretions. Suppositories for rectal application are usually prepared by mixing homogeneously active substances and excipients such as dispersing agents and emulsifying agents, dissolving or suspending uniformly in a base which is liquefied by warming, filling a constant volume of the resultant material into containers, and molding it into a shape and size. Lipophilic bases or hydrophilic bases are usually used.

(2) Semi-Solid Preparations for Rectal Application

Semi-solid preparations for rectal application are preparations which are in a form of cream, gel or ointment intended for application to around or inside of the anus. Semi-solid preparations for rectal application are usually prepared by emulsifying active substances with excipients in purified water and oil component such as Vaseline, or by homogeneously mixing active substances and excipients in a base of polymer gel or grease. Creams for rectal application are usually prepared by mixing homogeneously and emulsifying an oil-phase component (such as vaseline, fatty alcohols, etc.) and a water phase component (such as purified water with or without emulsifying agents or other suitable excipients), both warmed, of which either one contains the active substances. Gels for rectal application are gelatinous preparation. There are aqueous gels and oily gels. Aqueous gels are prepared adding polymers, other excipients and purified water to active substances, and dissolving or suspending, and gelatinizing by warming and cooling or by adding gelatinizing agents. Oily gels are prepared by adding liquid oily bases such as glycols, fatty alcohols and other excipients to active substances and mixing. Ointments for rectal application are semi-solid preparations, which dissolve or disperse active substances in a base. There are two types, hydrophobic ointment and hydrophilic ointments. Hydrophobic ointments are usually prepared by warming to melt hydrophobic bases such as fatty oils, waxes or paraffin, adding and mixing active substances in the bases to be dissolved or dispersed, and kneading the whole to make homogeneous. Hydrophilic ointments are usually prepared by warming to melt hydrophilic bases such as macrogol, adding and mixing active substances in the bases, and kneading the whole to make homogeneous.

(3) Enemas for Rectal Application

Enemas for rectal application are preparations in liquid form or viscous and gelatinous state, intended for applications via anus. Enemas for rectal application are preparations are usually prepared by dissolving or suspending active substances in purified water or suitable aqueous vehicle to make a given volume, and filling in containers. Dispersing agents, stabilizers and/or pH adjusting agents may be used.

[Preparations for Vaginal Application]

(1) Tablets for Vaginal Use

Tablets for vaginal use are solid preparations of a desired shapes and size, intended for application to the vagina, which release active substances by dissolving or dispersing gradually in the secretions. Tablets for vaginal use are usually prepared according to said preparation method of tablets.

(2) Suppositories for Vaginal Use

Suppositories for vaginal use are semi-solid preparations of a desired shapes and size, intended for application to the vagina, which release active substances by melting at body temperature or by dissolving or dispersing gradually in the secretions. Suppositories for vaginal use are usually prepared according to said preparation method of suppositories for rectal applications.

[Preparation for Cutaneous Application]

(1) Solid Preparations for Cutaneous Application

Solid preparations for cutaneous application are solid preparations intended for application to the skin (including scalp) or nails. Powders for cutaneous application are included in this category. Powders for cutaneous application are powdery solid preparations intended for external application. Powders for cutaneous application are usually prepared by mixing homogeneously active substances and excipients such as diluents and pulverizing the mixture.

(2) Liquids and Solutions for Cutaneous Application

Liquids and solutions for cutaneous application are liquid preparations intended for application to the skin (including scalp) or nails. Liniments and lotions are included in this category. Liquids and solutions for cutaneous application are usually prepared by mixing active substances and excipients in a vehicle, and filtering if necessary. Liniments are liquid or muddy preparations intended for external application to the skin by rubbing. Lotions are external liquids in which active substances are dissolved, emulsified or finely dispersed in an aqueous vehicle. Lotions are usually prepared by dissolving, suspending or emulsifying active substances in purified water with excipients and making homogeneous as a whole.

(3) Spray for Cutaneous Application

Spray for cutaneous application are preparations intended for spraying active substances onto the skin in mists, powders, forms or paste state. Spray for cutaneous application are classified into aerosols for cutaneous application and pump sprays for cutaneous application. Spray for cutaneous applications are usually prepared by dissolving or suspending active substances in a vehicle, filtering where necessary, and filling in containers. Aerosols for cutaneous application are sprays which atomize active substances together with liquefied or compressed gas filled in containers. Aerosols for cutaneous application are usually prepared by dissolving or suspending active substances in a vehicle, filling with liquefied propellants in pressure-resistant containers, and setting a continuous spray valve. If necessary, dispersing agents and stabilizer may be used. Pump sprays for cutaneous application are sprays which atomize active substances in containers by pumping. Pump sprays for cutaneous application are usually prepared by dissolving or suspending active substances with excipients in a vehicle, filling in containers and setting pumps to the containers.

(4) Ointments

Ointments are semi-solid preparations to be applied to the skin, which dissolve or disperse active substances in a base. There are two types, hydrophobic ointments and hydrophilic ointments. Hydrophobic ointments are usually prepared by warming to melt hydrophobic bases such as fatty oils, waxes or paraffin, adding and mixing active substances in the base to be dissolved or dispersed, and Kneading the whole to make homogeneous. Hydrophilic ointments are usually prepared by warming to melt hydrophilic bases such as macrogol, adding and mixing active substances in the bases, and kneading the whole to make homogenous.

(5) Creams

Creams are semi-solid preparations to be applied to the skin, which are in the form of oil-in-water or water-in-oil emulsions. Hydrophobic preparations in the form of water-in-oil emulsions may be termed "Oily creams". Creams are usually prepared by mixing homogeneously and emulsifying an oil-phase component and a water-phase component, both warmed, of which either one contains the active substances. There components have the following constituents. Oil-phase component: Vaseline, fatty alcohols, etc., with or without emulsifying agents or other suitable excipients. Water-phase component: purified water with or without emulsifying agents or other suitable excipients.

(6) Gels

Gels are gelatinous preparations intended for application to the skin. There are aqueous gels and oily gels. Aqueous gels are usually prepared by adding polymers, other excipients and purified water to active substances, dissolving or suspending, and gelatinizing by warming and cooling or by adding gelatinizing agents. Oily gels are usually prepared by adding liquid oily bases such as glycols, fatty alcohols and other excipients to active substances and mixing.

(7) Patches

Patches are preparations intended to be attached on the skin. Patches are classified into Tapes/Plasters and Cataplasms/Gel patches. Patches are usually prepared by mixing active substances homogeneously with a base such as a polymer or a mixture of polymers, spreading on a backing layer or liner, and cutting into a given size. Percutaneous absorption type preparations may be prepared by using a release rate-controlling membrane. Where necessary, adhesive agents or penetration enhancers may be used. Tapes/Plasters are patches which are prepared with bases of practically no water contain. Tapes/Plasters are usually prepared by mixing homogeneously active substances with or without excipients and a base of non-water-soluble natural or synthetic polymers such as resins, plastics or rubber, and spreading on a cloth or spreading and sealing on a cloth or plastic film, cutting into a given size. The preparations may be also prepared by filling a mixture of active substances and a base with or without other excipients in releasers composed with a release-controlling film, supporter and liner. Cataplasms/Gels are patches using water containing bases. Cataplasms/Gels patches are usually prepared by mixing active substances, purified water, and glycerin or other liquid materials, or by mixing and kneading natural or synthetic polymers, which are soluble in water or absorbent of water, with purified water, adding active substances, mixing the whole homogeneously, spreading on a cloth or film, and cutting into a given size.

EXAMPLES

The present invention is described in details by referring to Examples hereinbelow, but the present invention is not limited to Examples.

Concerning chromatographic separation and TLC, a solvent in parentheses corresponds to an eluting solvent or a developing solvent employed and a ratio is expressed by volume ratio.

Concerning NMR, a solvent in parentheses corresponds to a solvent used for the measurement.

LC-MS/ELSD was performed under the following condition:

Condition 1

{column: Waters ACQUITY $C_{18}$ (particle size: $1.7 \times 10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (the ratio of mobile phase (A):mobile phase (B) is described): [0 min] 95:5; [0.1 min] 95:5; [1.2 min] 5:95; [1.4 min] 5:95; [1.41 min] 95:5; [1.5 min] 95:5; Detector: UV(PDA), ELSD, MS}

Condition 2

{column: YMC Triart $C_{18}$ (particle size: $1.9 \times 10^{-6}$ m; column length: 30×2.0 mm I.D.); flow rate: 1.0 ml/min; column temperature: 30° C.; mobile phase (A): 0.1% trifluoroacetic acid aqueous solution; mobile phase (B): 0.1% trifluoroacetic acid aqueous-acetonitrile solution; gradient (the ratio of mobile phase (A):mobile phase (B) is described): [0 min] 95:5; [0.1 min] 95:5; [1.2 min] 5:95; [1.4 min] 5:95; [1.41 min] 95:5; [1.5 min] 95:5; Detector: UV(PDA), ELSD, MS}

A compound name used in the present specification was given by using a computer program ACD/Name (registered trademark) which generally denominates a compound according to the IUPAC nomenclature, by using Chemdraw Ultra (Version 12.0, supplied by Cambridge Soft) or by denominating according to the IUPAC nomenclature.

Reference Example 1: N,N-dibenzyl-N'-tert-butyl-2-chloro-5-nitropyrimidine-4,6-diamine

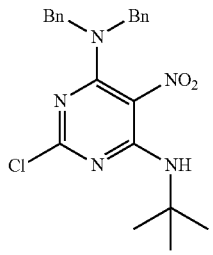 [SMILES: CC(C)(C)Nc1nc(Cl)nc(N(Cc2ccccc2)Cc2ccccc2)c1[N+](=O)[O-]]

To 2,4,6-trichloro-5-nitropyrimidine (CAS No. 4359-87-9, 22.8 g) in methylene chloride(170 mL), a solution of tert-butylamine (7.3 g) in methylene chloride (30 mL) was slowly added dropwise at 0° C. To the reaction mixture, diisopropylethylamine (17.3 mL) was slowly added dropwise at 0° C. The reaction mixture was stirred at 0° C. for 60 minutes. To the reaction mixture, water was poured and the reaction mixture was extracted with methylene chloride. The obtained organic layer was washed with a saturated saline solution, and was dried over sodium sulfate, and thereafter, was concentrated under a reduced pressure. 12.7 g of the obtained intermediate (27.8 g) was dissolved in methylene chloride (170 mL). To the solution, a solution of dibenzylamine (19.2 mL) in methylene chloride (30 mL) was added dropwise at 0° C. To the reaction mixture, diisopropylethylamine (17.3 mL) was added dropwise at 0° C. The reaction mixture was stirred at 0° C. for 60 minutes. To the reaction mixture, water was poured and the reaction mixture was extracted with methylene chloride. The obtained organic layer was washed with a saturated saline solution, and was dried over sodium sulfate, and thereafter, was concentrated under a reduced pressure. The remaining intermediate (15.09 g) was similarly reacted. The obtained crude product was purified by silica gel column chromatography to give the title compound (27.2 g) having the following physical properties.

TLC: Rf 0.45 (hexane:ethyl acetate=9:1);

$^1$H-NMR (CDCl$_3$): δ1.51, 4.52, 7.06-7.14, 7.23-7.38, 8.41.

Reference Example 2: 9-tert-butyl-2-chloro-6-(dibenzylamino)-7,9-dihydro-8H-purin-8-one

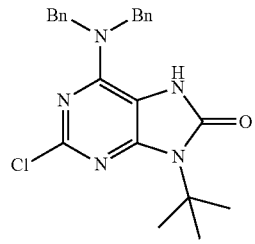 [SMILES: CC(C)(C)n1c(=O)[nH]c2c(N(Cc3ccccc3)Cc3ccccc3)nc(Cl)nc21]

Ammonium chloride (20.8 g) was dissolved in water (156 mL), and was mixed with zinc (42.4 g). To this suspension, a solution of the compound prepared in Reference Example 1 (27.6 g) in ethyl acetate (467 mL) was added dropwise at room temperature, and the mixture was stirred at room temperature for 4 hours. The reaction mixture was filtered through Celite (trade name), and Celite was washed with water and ethyl acetate. The filtrate was extracted with ethyl acetate. The obtained organic layer was washed with water and saturated saline solution, and was dried over sodium sulfate, and thereafter, was concentrated under a reduced pressure. To the obtained residue, tetrahydrofuran (276 mL) was added. To the resulting solution, 1,1'-carbonyldiimidazole (22.3 g) and diazabicycloundecene (DBU; 10.3 mL) were added. The reaction mixture was stirred at room temperature for 1 hour. To the reaction mixture, 1 N hydrochloric acid was added, and the mixture was extracted with ethyl acetate. The obtained organic layer was washed with water, saturated aqueous sodium hydrogen carbonate solution and saturated saline solution. The obtained organic layer was dried over sodium sulfate, and thereafter, was concentrated under a reduced pressure. The obtained residue was washed with methyl-tert-butyl ether (MTBE), and was filtrated. The filtrate was dried to give the title compound (23.3 g) having the following physical properties were obtained.

TLC: Rf 0.40 (hexane:ethyl acetate=4:1);

$^1$H-NMR (CDCl$_3$): δ1.70, 4.76, 7.22-7.40, 8.16.

Reference Example 3: 9-tert-butyl-6-(dibenzylamino)-2-{[2-fluoro-4-(methylsulfonyl) phenyl]amino}-7,9-dihydro-8H-purin-8-one

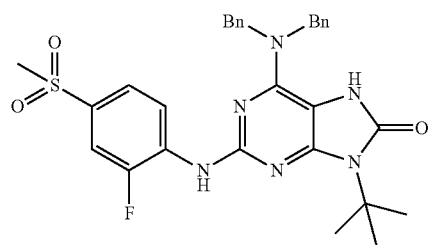 [SMILES: CC(C)(C)n1c(=O)[nH]c2c(N(Cc3ccccc3)Cc3ccccc3)nc(Nc3ccc(S(C)(=O)=O)cc3F)nc21]

To a suspended solution of the compound (127 mg) prepared in Reference Example 2, 2-fluoro-4-methylsulfonylaniline (62 mg) and cesium carbonate (293 mg) in dimethoxyethane (0.9 mL) was degassed, and was purged with argon. 2-(dicyclohexylphosphino)-2',4', 6'-triisopropylbiphenyl (29 mg) and tris (dibenzylideneacetone)dipalladium (0) (28 mg) were added. The reaction mixture was stirred at 85° C. for 16 h. To the reaction mixture, water was added and the mixture was extracted with ethyl acetate. The obtained organic layer was washed with saturated saline. The obtained organic layer was dried over sodium sulfate, and was concentrated under a reduced pressure. The obtained residue was purified by silica gel column chromatography to give the title compound (153 mg) having the following physical properties.

TLC: Rf 0.23 (hexane:ethyl acetate=2:1);
$^1$H-NMR (CDCl$_3$): δ1.72, 3.02, 4.82, 7.15-7.18, 7.22-7.39, 7.41-7.45, 7.57-7.62, 8.45-8.52, 9.07.

Reference Example 4: 6-amino-9-tert-butyl-2-{[2-fluoro-4-(methylsulfonyl)phenyl] amino}-7,9-dihydro-8H-purin-8-one

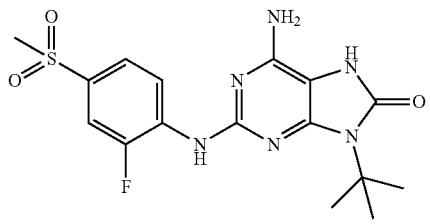 [SMILES: CC(C)(C)n1c(=O)[nH]c2c(N)nc(Nc3ccc(S(C)(=O)=O)cc3F)nc21]

Under a nitrogen atmosphere, the compound (163 mg) prepared in Reference Example 3 was dissolved in ethanol (1.1 mL) and tetrahydrofuran (0.3 mL), and 20% palladium hydroxide carbon (80 mg) was added. Under a hydrogen atmosphere, the reaction mixture was stirred at 60° C. for 6 hours, and thereafter, was filtered through Celite (trade name), and Celite was washed with methylene chloride/methanol. The filtrate was concentrated under reduced pressure. The resulting residue was solidified with ethyl acetate, and the solid was filtrated. The filtrate was dried to give the compound of the present invention (62 mg) having the following physical properties.

TLC: Rf 0.47 (methylene chloride:methanol=9:1);
$^1$H-NMR (DMSO-d$_6$): δ1.70, 3.20, 6.35, 7.59-7.64, 7.67-7.72, 8.41-8.48, 9.92.

Reference Example 5: 4-bromo-7-fluoro-1-(tetrahydro-2H-pyran-2-yl)-1H-indazole

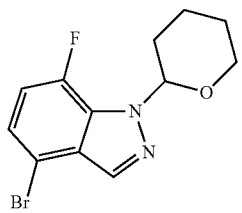 [SMILES: Fc1ccc(Br)c2cnn(C3CCCCO3)c12]

To a solution of 4-bromo-7-fluoro-1H-indazole (918 mg) in methylene chloride (14 mL), 3,4-dihydro-2H-pyran (1.56 mL) and paratoluenesulfonic acid monohydrate (81 mg) was added. The reaction mixture was stirred at 40° C. for 1.5 hours. To the reaction mixture, a saturated sodium bicarbonate aqueous solution was added, and was extracted with ethyl acetate. The obtained organic layer was washed with a saturated saline solution, and was dried over anhydrous sodium sulfate, and thereafter, was distilled off under a reduced pressure. The obtained residue was purified by silica gel column chromatography to give the title compound (1.24 g) having the following physical properties.

TLC: Rf 0.61 (hexane:ethyl acetate=5:1);
$^1$H-NMR (CDCl$_3$): δ1.48-1.82, 2.03-2.23, 2.51-2.68, 3.69-3.80, 4.00-4.08, 5.83-5.90, 6.91-7.00, 7.17-7.23, 8.03-8.06.

Reference Example 6: [7-fluoro-1-(tetrahydro-2H-pyran-2-yl)-1H-indazol-4-yl]boronic acid

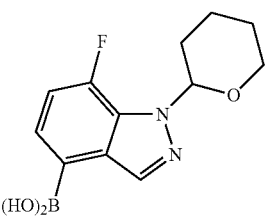 [SMILES: OB(O)c1ccc(F)c2c1cnn2C1CCCCO1]

Under a nitrogen atmosphere, the compound (1.24 g) prepared in Reference Example 5 and triisopropylborate (3.8 mL) were dissolved in tetrahydrofuran (16.6 mL), and was cooled to −78° C. To the solution, n-butyllithium (8.02 mL, 1.55 M/hexane) was added dropwise. The reaction mixture was stirred at −40° C. for 1 hours. To the reaction solution, water was added, and the organic layer was back-extracted with 0.5 N aqueous sodium hydroxide solution. To the obtained aqueous layer, ammonium acetate (1.39 g) was added, and was stirred at room temperature for 30 minutes. The reaction solution was cooled to 0° C. To the reaction mixture, sodium dihydrogenphosphate was added, and pH was adjusted to 4 to 5.

The precipitated solid was filtrated. The filtrate was washed with cold water and was dried, and thereafter, to give the compound of the present invention (710 mg) having the following physical properties.

TLC: Rf 0.34 (hexane:ethyl acetate=2:1);
$^1$H-NMR (DMSO-d$_6$): δ1.47-1.60, 1.63-1.82, 1.97-2.10, 1.97-2.10, 2.35-2.54, 3.58-3.69, 3.83-3.94, 5.79-5.85, 7.18-7.27, 7.58-7.64, 8.27, 8.34-8.37.

Reference Example 7: 6-amino-9-tert-butyl-2-{[2-fluoro-4-(methylsulfonyl)phenyl] amino}-7-[7-fluoro-1-(tetrahydro-2H-pyran-2-yl)-1H-indazol-4-yl]-7,9-dihydro-8H-purin-8-one

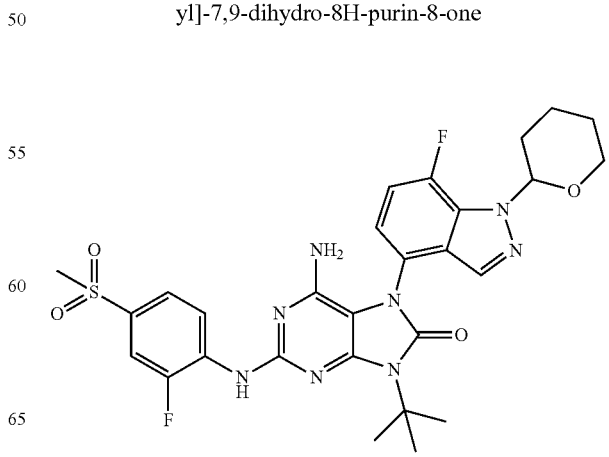

The compound prepared in Reference Example 4 (45 mg), the compound prepared in Reference Example 6 (60 mg), copper acetate (Cu (OAc)$_2$) (41 mg) and a solution of triethylamine (64 μL) in acetonitrile was stirred at 40° C. for 20 hours.

To the reaction mixture, ammonia water was added, and was extracted with ethyl acetate. The obtained organic layer was washed with a saturated saline solution, and was dried over sodium sulfate, and thereafter, was concentrated under a reduced pressure. The obtained residue was purified by silica gel column chromatography to give the title compound (19 mg) having the following physical properties.

TLC: Rf 0.53 (hexane:ethyl acetate=1:2);

$^1$H-NMR (CDCl$_3$): δ1.55-1.84, 1.89, 2.04-2.24, 2.48-2.69, 3.06, 3.69-3.86, 3.97-4.16, 4.18-4.29, 5.88-5.97, 7.03-7.12, 7.16-7.27, 7.62-7.74, 7.92-8.01, 8.73-8.80.

Example 1: 6-amino-7-(7-fluoro-1H-indazol-4-yl)-2-{[2-fluoro-4-(methylsulfonyl) phenyl]amino}-9-(2-methyl-2-propanyl)-7,9-dihydro-8H-purin-8-one

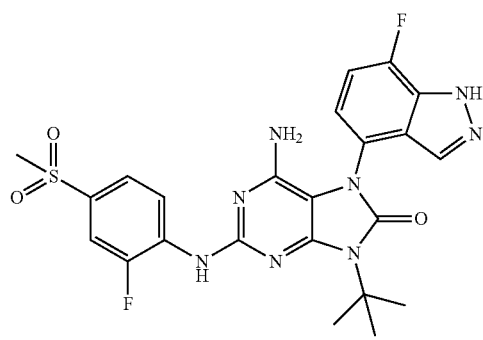 [SMILES: CC(C)(C)n1c(=O)n(-c2ccc(F)c3[nH]ncc23)c2c(N)nc(Nc3ccc(S(C)(=O)=O)cc3F)nc21]

The compound (40 mg) prepared in Reference Example 7 was dissolved in methanol (0.5 mL). To the solution, 4 N hydrochloric acid/dioxane (1 mL) was added at room temperature. The reaction mixture was stirred at room temperature for 1 hour, and thereafter, saturated aqueous sodium hydrogen carbonate solution was added. The reaction mixture was extracted with ethyl acetate. The obtained organic layer was washed with a saturated saline solution, and was dried over sodium sulfate, and thereafter, was concentrated under a reduced pressure. The obtained residue was washed with hexane, and was filtrated. The filtrate was dried to give the compound of the present invention (10 mg) having the following physical properties.

TLC: Rf 0.58 (hexane:ethyl acetate=1:2);

$^1$H-NMR (CDCl$_3$): δ1.91, 3.07, 4.24, 7.07-7.12, 7.17-7.24, 7.63-7.76, 8.02-8.05, 8.73-8.81.

Examples 2

A similar procedure to Reference Example 1→Reference Example 2→Reference Example 3→Reference Example 4→Reference Example 7→Example 1 was carried out by using isopropylamine instead of tert-butylamine, and using a corresponding boronic acid instead of the compound prepared in Reference Example 6 to give the compound of the present invention having the following physical properties.

Example 2-1: 6-amino-7-(7-chloro-1H-indazol-4-yl)-2-{([2-fluoro-4-(methylsulfonyl) phenyl]amino}-9-isopropyl-7,9-dihydro-8H-purin-8-one

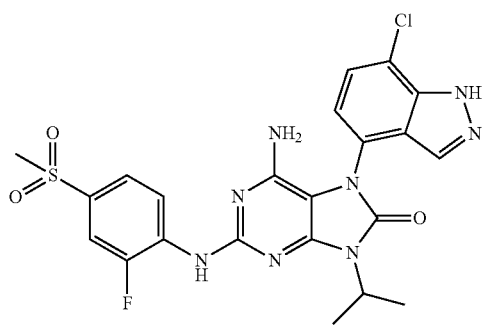

TLC: Rf 0.37 (hexane:ethyl acetate=2:3);

$^1$H-NMR (CDCl$_3$): δ1.62-1.74, 3.07, 4.35, 4.78-4.88, 7.08-7.14, 7.28-7.35, 7.49-7.54, 7.64-7.80, 8.11, 8.80-8.87.

Example 2-2: 6-amino-7-(6,7-difluoro-1H-indazol-4-yl)-2-{[2-fluoro-4-(methylsulfonyl)phenyl]amino}-9-isopropyl-7,9-dihydro-8H-purin-8-one

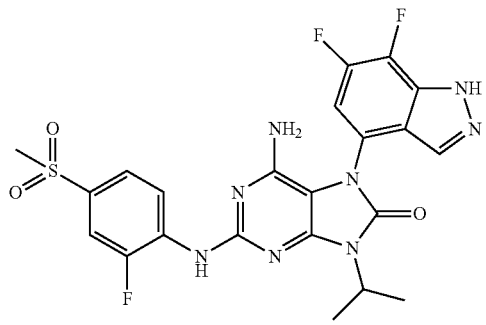 [SMILES: CC(C)n1c(=O)n(-c2cc(F)c(F)c3[nH]ncc23)c2c(N)nc(Nc3ccc(S(C)(=O)=O)cc3F)nc21]

TLC: Rf 0.30 (ethyl acetate);

$^1$H-NMR (CDCl$_3$): δ1.60-1.80, 3.07, 4.41, 4.77-4.91, 7.03-7.11, 7.30-7.38, 7.62-7.68, 7.69-7.78, 7.98-8.02, 8.78-8.85.

Example 3: 6-amino-7-(7-fluoro-1H-indazol-4-yl)-2-{[2-fluoro-4-(methylsulfonyl) phenyl]amino}-9-isopropyl-7,9-dihydro-8H-purin-8-one A similar procedure to Reference Example 1→Reference Example 2→Reference Example 3→Reference Example 4→Reference Example 7→Example 1 was carried out by using isopropylamine instead of tert-butylamine to give the compound of the present invention having the following physical properties.

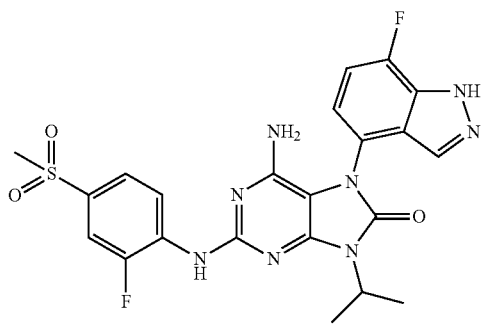 [SMILES: CC(C)n1c(=O)n(-c2ccc(F)c3[nH]ncc23)c2c(N)nc(Nc3ccc(S(C)(=O)=O)cc3F)nc21]

TLC: Rf 0.40 (hexane:ethyl acetate=1:4);

$^1$H-NMR (CDCl$_3$): δ1.62-1.72, 3.07, 4.33, 4.79-4.92, 7.07-7.14, 7.17-7.25, 7.30-7.35, 7.64-7.69, 7.72-7.78, 8.04-8.08, 8.80-8.88.

Reference Example 8: 2-chloro-N,N-bis(4-methoxybenzyl)-5-nitro-N'-(propan-2-yl) pyrimidine-4,6-diamine

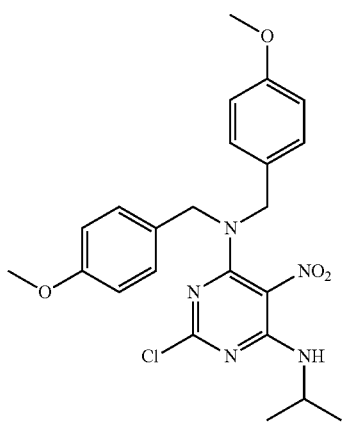 [SMILES: COc1ccc(CN(Cc2ccc(OC)cc2)c2nc(Cl)nc(NC(C)C)c2[N+](=O)[O-])cc1]

To a solution of 2,4,6-trichloro-5-nitropyrimidine (4 g) in methylene chloride (130 mL), bis (4-methoxybenzyl) amine (4.5 g) and triethylamine (2.4 mL) in methylene chloride (20 mL) was slowly added dropwise at 0° C. The reaction mixture was stirred at 0° C. for 30 minutes. To the reaction mixture, isopropylamine (1.7 mL) and triethylamine (2.7 mL) in a solution of methylene chloride (20 mL) was added dropwise at 0° C. The reaction mixture was stirred for 120 minutes. To the reaction mixture, water was poured and was extracted with methylene chloride. The obtained organic layer was washed with saturated saline solution, and was dried over magnesium sulfate, and thereafter, was concentrated under reduced pressure. The resulting residue was stirred in hexane/MTBE (4/1) for 30 minutes. The precipitated solid was filtrated. The filtrate was dried to give the title compound (7.8 g) having the following physical properties.

TLC: Rf 0.41 (hexane:ethyl acetate=5:1);

$^1$H-NMR (CDCl$_3$): δ1.24-1.30, 3.80, 4.37-4.50, 6.79-6.85, 6.97-7.03, 8.18-8.24.

Reference Example 9: 2-chloro-6-[bis(4-methoxybenzyl)amino]-9-(propan-2-yl)-7,9-dihydro-8H-purin-8-one

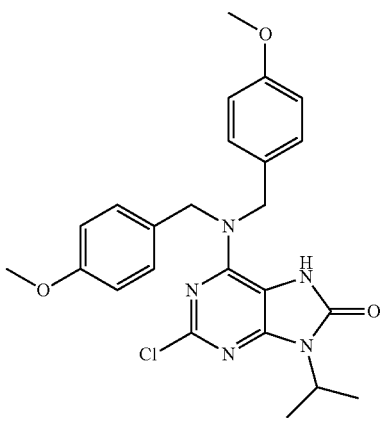 [SMILES: COc1ccc(CN(Cc2ccc(OC)cc2)c2nc(Cl)nc3c2[nH]c(=O)n3C(C)C)cc1]

Ammonium chloride (5.4 g) was dissolved in water (30 mL), and was mixed with zinc (11 g). To this suspension, a solution of the compound (7.8 g) prepared in Reference Example 8 in ethyl acetate (200 mL) was added dropwise at room temperature. The reaction mixture was stirred at room temperature for 5 hours.
The reaction mixture was filtered through Celite (trade name), and Celite was washed with water and ethyl acetate. The resulting filtrate was extracted with ethyl acetate. The obtained organic layer was washed with water and saturated saline solution, and was dried over magnesium sulfate, and thereafter, was concentrated under reduced pressure. To a solution of the obtained residue in tetrahydrofuran (150 mL), 1,1'-carbonyldiimidazole (5 g) and DBU (2.3 mL) were added. The reaction mixture was stirred at room temperature for 20 hours. To the reaction mixture, 1 N hydrochloric acid was added and was extracted with ethyl acetate. The obtained organic layer was washed with 1N hydrochloric acid, saturated aqueous sodium hydrogen carbonate solution and saturated saline solution. The obtained organic layer was dried over magnesium sulfate, and thereafter, was concentrated under reduced pressure. The obtained residue was stirred in hexane/ethyl acetate (2/1) for 20 minutes and was filtrated. The filtrate was dried to give the title compound (5.9 g) having the following physical properties.

TLC: Rf 0.34 (hexane:ethyl acetate=2:1);

$^1$H-NMR (CDCl$_3$): δ1.38-1.48, 3.80, 4.55-4.74, 6.80-6.92, 7.09-7.21, 8.39.

Reference Example 10: 2-[(4-acetyl-2-fluorophenyl)amino]-6-[bis(4-methoxybenzyl) amino]-9-(propan-2-yl)-7,9-dihydro-8H-purin-8-one

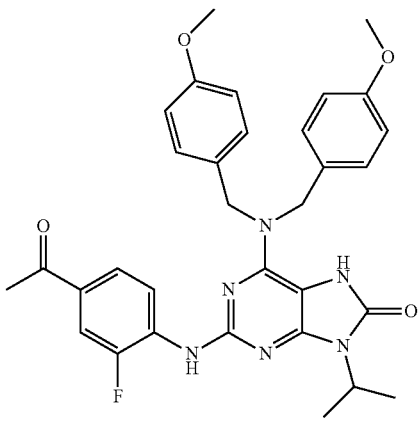 [SMILES: COc1ccc(CN(Cc2ccc(OC)cc2)c2nc(Nc3ccc(C(C)=O)cc3F)nc3c2[nH]c(=O)n3C(C)C)cc1]

The compound prepared in Reference Example 9 (3 g), 1-(4-amino-3-fluorophenyl) ethanone (1.1 g) and a solution of cesium carbonate (6.3 g) in dimethoxyethane (21 mL)/tert-butanol) was degassed and was purged with argon. To this reaction mixture, 2-(dicyclohexylphosphino)-2',4',6'-triisopropylbiphenyl (310 mg) and tris (dibenzylideneacetone) dipalladium (0) (290 mg) was added. The reaction mixture was stirred at 90° C. for 4 hours. Further, 2-(dicyclohexylphosphino)-2',4', 6'-triisopropylbiphenyl (155 mg) and tris (dibenzylideneacetone) dipalladium (0) (145 mg) were added. The reaction mixture was stirred at 90° C. for 4 hours. The reaction mixture was filtered through Celite (trade name). Celite was washed with ethyl acetate. The obtained filtrate was concentrated under reduced pressure. The obtained residue was purified by silica gel column chromatography. The obtained crude product was washed with MTBE, and was filtrated. The filtrate was dried to give the title compound (2.4 g) having the following physical properties.

TLC: Rf 0.28 (hexane:ethyl acetate=3:2);
$^1$H-NMR (CDCl$_3$): δ1.54-1.61, 2.54, 3.81, 4.60-4.78, 6.86-6.93, 7.16-7.26, 7.56-7.61, 7.65-7.71, 8.48-8.56.

Reference Example 11: 2-[(4-acetyl-2-fluorophenyl)amino]-6-amino-9-(propan--2-yl)-7,9-dihydro-8H-purin-8-one

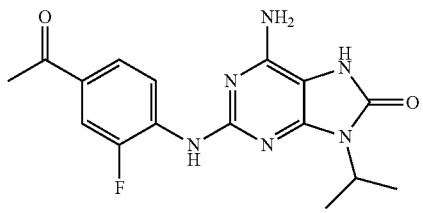 [SMILES: CC(=O)c1ccc(Nc2nc(N)c3[nH]c(=O)n(C(C)C)c3n2)c(F)c1]

The compound (1.7 g) prepared in Reference Example 10 was dissolved in methylene chloride (5 mL) and trifluoroacetic acid (5 mL). The reaction mixture was stirred at 60° C. for 3 hours. The reaction mixture was concentrated under reduced pressure. To the obtained residue, a saturated aqueous solution of sodium bicarbonate was added, and was extracted with ethyl acetate/tetrahydrofuran. The obtained organic layer was washed with saturated saline solution, and was dried over magnesium sulfate, and thereafter, was concentrated under reduced pressure. The obtained residue was washed with hexane/ethyl acetate (1/1) and was filtrated. The filtrate was washed with methylene chloride and was filtrated. The filtrate was dried to give the title compound (0.55 g) having the following physical properties.

TLC: Rf 0.60 (ethyl acetate);
$^1$H-NMR (DMSO-d$_6$): δ1.42-1.49, 2.54, 4.42-4.56, 6.36, 7.65-7.78, 8.35-8.40, 8.42-8.51, 9.88.

Examples 4: 2-[(4-acetyl-2-fluorophenyl)amino]-6-amino-7-(1H-indazol--4-yl)-9-isopropyl-7,9-dihydro-8H-purin-8-one

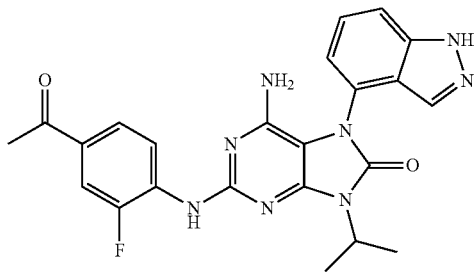 [SMILES: CC(=O)c1ccc(Nc2nc(N)c3c(n2)n(C(C)C)c(=O)n3-c2cccc3[nH]ncc23)c(F)c1]

A similar procedure to Reference Example 7→Example 1 was carried out by using the compound prepared in Reference Example 11 instead of the compound prepared in Reference Example 4 and using [1-(tetrahydro-2H-pyran-2-yl)-1H-indazol-4-yl] boronic acid instead of the compound prepared in Reference Example 6 to give the compound of the present invention having the following physical properties.

TLC: Rf 0.22 (hexane:ethyl acetate=1:4);
$^1$H-NMR (DMSO-d$_6$): δ1.53-1.60, 2.53, 4.60-4.72, 5.49, 7.06-7.10, 7.44-7.51, 7.61-7.65, 7.69-7.79, 7.95, 8.44-8.52, 8.60-8.62, 13.32.

Examples 5

A similar procedure to Reference Example 1→Reference Example 2→Reference Example 3→Reference Example 4→Reference Example 7→Example 1 was carried out by using the corresponding amine instead of tert-butylamine and using the corresponding amine compound instead of 2-fluoro-4-(methylsulfonyl) aniline and using the corresponding boronic acid instead of the compound prepared in Reference Example 6 to give the compound of the present invention having the following physical properties. In Examples 5-1, 5-5 and 5-17, HPLC preparative purification (mobile phase (A): 0.1% trifluoroacetic acid aqueous solution; mobile phase (B): 0.1% trifluoroacetic acid—acetonitrile) was performed with an eluent containing trifluoroacetic acid, the compound of the present invention was obtained as a trifluoroacetate salt.

Examples 5-1: 6-amino-9-cyclopentyl-2-{[2-fluoro-4-(methylsulfonyl)phenyl]amino}-7-(1H-indazol-4-yl)-7,9-dihydro-8H-purin-8-one trifluoroacetate

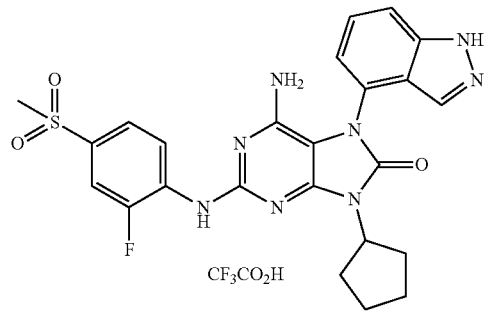 [SMILES: CS(=O)(=O)c1ccc(Nc2nc(N)c3c(n2)n(C2CCCC2)c(=O)n3-c2cccc3[nH]ncc23)c(F)c1 ; "CF3CO2H"]

Purity (LC-MS/ELSD) Condition 1: 70% (Retention time: 0.85 minutes);
MASS (ESI, Pos.): δ23 (M+H)$^+$;
$^1$H-NMR (DMSO-d$_6$): δ1.55-1.69, 1.80-2.02, 2.16-2.35, 3.22, 4.71-4.84, 5.53, 7.04-7.09, 7.44-7.51, 7.61-7.66, 7.71-7.76, 7.96, 8.51-8.58, 8.78.

Examples 5-2: 6-amino-9-cyclobutyl-2-{[2-fluoro-4-(methylsulfonyl)phenyl]amino}-7-(1H-indazol-4-yl)-7,9-dihydro-8H-purin-8-one TLC: Rf 0.26 (hexane:ethyl acetate=1:4);
Purity (LC-MS/ELSD) Condition 1: 99.8% (Retention time: 0.84 minutes);
MASS (ESI, Pos.): 509 (M+H)$^+$.

Examples 5-3: 6-amino-2-{[2$^2$-fluoro-4-(methylsulfonyl)phenyl]amino}-7-(1H-indazol-4-yl)-9-(2-methyl-2-propanyl)-7,9-dihydro-8H-purin-8-one TLC: Rf 0.20 (hexane:ethyl acetate=1:2);
Purity (LC-MS/ELSD) Condition 1: 97.5% (Retention time: 0.85 minutes);
MASS (ESI, Pos.): 511 (M+H)$^+$;
$^1$H-NMR (CDCl$_3$): δ1.92, 3.07, 4.29, 7.15-7.18, 7.23-7.28, 7.46-7.58, 7.63-7.76, 8.02, 8.74-8.82.

Examples 5-4: 6-amino-2-{[2-fluoro-4-(methyl-sulfonyl)phenyl]amino}-9-isopropyl-7-(7-methyl-1H-indazol-4-yl)-7,9-dihydro-8H-purin-8-one TLC: Rf 0.27 (hexane:ethyl acetate=1:4);
Purity (LC-MS/ELSD) Condition 1: 99.6% (Retention time: 0.83 minutes);
MASS (ESI, Pos.): 511 (M+H)+;
$^1$H-NMR (CD$_3$OD): δ1.63-1.70, 2.65, 3.12, 4.77-4.95, 7.08-7.11, 7.30-7.35, 7.65-7.75, 7.96, 8.86-8.94.

Examples 5-5: 6-amino-9-(3,3-difluorocyclopentyl)-2-{[2-fluoro-4-(methylsulfonyl) phenyl]amino}-7-(1H-indazol-4-yl)-7,9-dihydro-8H-purin-8-one trifluoroacetate

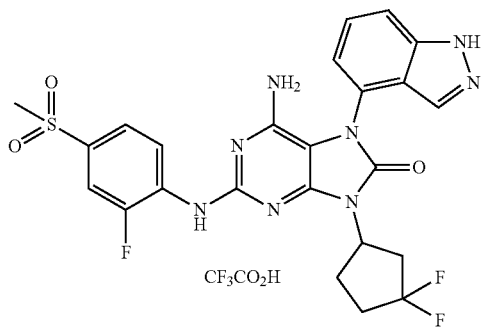 [SMILES: CS(=O)(=O)c1ccc(Nc2nc(N)c3c(n2)n(C2CCC(F)(F)C2)c(=O)n3-c2cccc3[nH]ncc23)c(F)c1 ; "CF3CO2H"]

Purity (LC-MS/ELSD) Condition 1: 99.9% (Retention time: 0.85 minutes);
MASS (ESI, Pos.): 559 (M+H)+;
$^1$H-NMR (DMSO-d$_6$): δ2.12-2.23, 2.48-2.58, 2.97-3.12, 3.21, 4.94-5.02, 5.57, 7.08-7.11, 7.47-7.52, 7.62-7.66, 7.73-7.76, 8.00, 8.51-8.54, 8.83, 13.35.

Examples 5-6: 6-amino-7-(7-chloro-1H-indazol-4-yl)-9-isopropyl-2-{[2-methoxy-4-(methylsulfonyl)phenyl]amino}-7,9-dihydro-8H-purin-8-one TLC: Rf 0.25 (ethyl acetate);
Purity (LC-MS/ELSD) Condition 1: 96.5% (Retention time: 0.88 minutes);
MASS (ESI, Pos.): 543 (M+H)+;
$^1$H-NMR (CDCl$_3$): δ1.66-1.72, 3.07, 4.01, 4.32, 4.78-4.91, 7.08-7.12, 7.38-7.40, 7.49-7.52, 7.58-7.62, 7.72, 8.11, 8.77-8.80.

Examples 5-7: 6-amino-7-(7-fluoro-1H-indazol-4-yl)-2-{[2-methoxy-4-(methylsulfonyl)phenyl]amino}-9-(2-methyl-2-propanyl)-7,9-dihydro-8H-purin-8-one

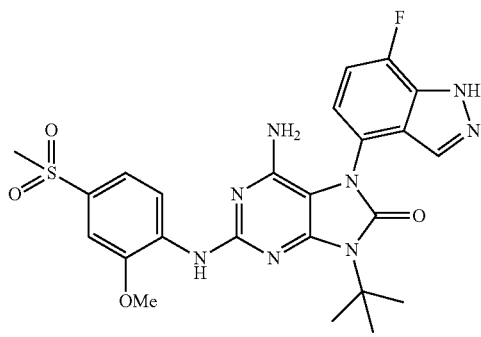 [SMILES: COc1cc(S(C)(=O)=O)ccc1Nc1nc(N)c2c(n1)n(C(C)(C)C)c(=O)n2-c1ccc(F)c2[nH]ncc12]

Purity (LC-MS/ELSD) Condition 1: 99.9% (Retention time: 0.88 minutes);
MASS (ESI, Pos.): 541 (M+H)+;
$^1$H-NMR (CDCl$_3$): δ1.92, 3.07, 4.01, 4.22, 7.07-7.12, 7.16-7.23, 7.37-7.39, 7.55-7.60, 7.66, 8.03-8.05, 8.68-8.72.

Examples 5-8: 6-amino-2-{[2-fluoro-4-(methyl-sulfonyl)phenyl]amino}-7-(1H-indol-6-yl)-9-(tetra-hydro-3-furanyl)-7,9-dihydro-8H-purin-8-one TLC: Rf 0.57 (ethyl acetate);
$^1$H-NMR (CD$_3$OD): δ2.33-2.45, 2.51-2.63, 3.11, 3.87-3.97, 4.05-4.14, 4.24-4.34, 5.17-5.27, 6.56-6.58, 7.06-7.11, 7.39-7.41, 7.52-7.54, 7.63-7.75, 8.94-9.01.

Examples 5-9: 6-amino-9-cyclopentyl-2-{[2-fluoro-4-(methylsulfonyl)phenyl]amino}-7-(3-hydroxyphenyl)-7,9-dihydro-8H-purin-8-one

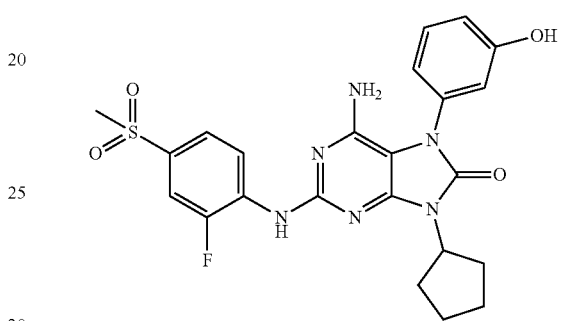

Purity (LC-MS/ELSD) Condition 1: 99.8% (Retention time: 0.89 minutes);
MASS (ESI, Pos.): 499 (M+H)+;
$^1$H-NMR (CDCl$_3$): δ1.69-1.80, 1.99-2.11, 2.31-2.43, 3.07, 4.48, 4.83-4.94, 5.81, 6.87-6.96, 6.97, 7.35-7.40, 7.64-7.74, 8.80-8.85.

Examples 5-10: 6-amino-2-{[2,3-difluoro-4-(methylsulfonyl)phenyl]amino}-7-(7-fluoro-11H-indazol-4-yl)-9-isopropyl-7,9-dihydro-8H-purin-8-one TLC: Rf 0.30 (ethyl acetate);
Purity (LC-MS/ELSD) Condition 1: 97.5% (Retention time: 0.86 minutes);
MASS (ESI, Pos.): 533 (M+H)+;
$^1$H-NMR (CDCl$_3$): δ1.64-1.71, 3.23, 4.34, 4.78-4.90, 7.06-7.15, 7.18-7.25, 7.27-7.32, 7.66-7.74, 8.04-8.08, 8.56-8.63.

Examples 5-11: 6-amino-2-{[2-difluoro-4-(methyl-sulfonyl)phenyl]amino}-7-(7-fluoro-1H-indazol-4-yl)-9-isopropyl-7,9-dihydro-8H-purin-8-one Purity (LC-MS/ELSD) Condition 1: 99.6% (Retention time: 0.86 minutes);
MASS (ESI, Pos.): 533 (M+H)+;
$^1$H-NMR (CDCl$_3$): δ1.64-1.73, 3.23, 4.35, 4.78-4.88, 7.07-7.13, 7.18-7.23, 7.29-7.39, 7.61-7.69, 8.05-8.08, 8.64-8.73, 10.48-10.65.

Examples 5-12: 6-amino-7-(3-amino-4-fluorophenyl)-2-{[2-fluoro-4-(methylsulfonyl) phenyl]amino}-9-isopropyl-7,9-dihydro-8H-purin-8-one

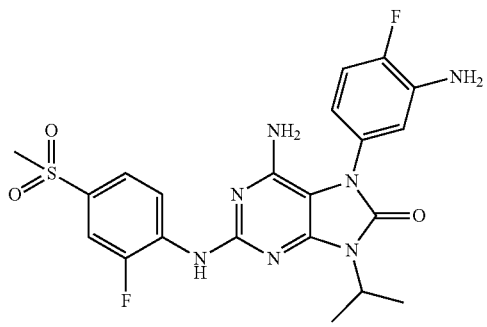 [SMILES: CC(C)n1c(=O)n(-c2ccc(F)c(N)c2)c2c(N)nc(Nc3ccc(S(C)(=O)=O)cc3F)nc21]

TLC: Rf 0.50 (hexane:ethyl acetate=3:7);

$^1$H-NMR (CD$_3$OD): δ1.57-1.63, 3.11, 4.69-4.82, 6.61-6.69, 6.85-6.91, 7.07-7.16, 7.63-7.73, 8.83-8.92.

Examples 5-13: 6-amino-7-(1-benzofuran-5-yl)-2-{[2-fluoro-4-(methylsulfonyl) phenyl]amino}-9-isopropyl-7,9-dihydro-8H-purin-8-one

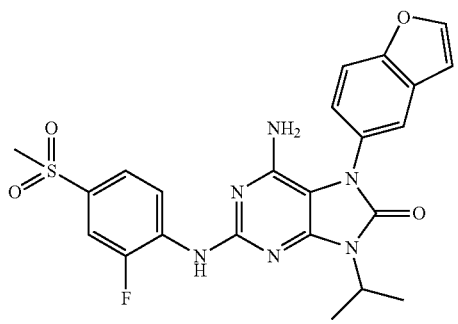 [SMILES: CC(C)n1c(=O)n(-c2ccc3occc3c2)c2c(N)nc(Nc3ccc(S(C)(=O)=O)cc3F)nc21]

TLC: Rf 0.31 (hexane:ethyl acetate=1:1);

$^1$H-NMR (CDCl$_3$): δ1.63-1.72, 3.07, 4.36, 4.76-4.89, 6.83-6.86, 7.24-7.31, 7.34-7.39, 7.61-7.78, 8.81-8.89.

Examples 5-14: 6-amino-2-{[2-fluoro-4-(methylsulfonyl) phenyl]amino}-7-(1H-indazol-4-yl)-9-(1,1,1-trifluoro-2-propanyl)-7,9-dihydro-8H-purin-8-one TLC: Rf 0.60 (ethyl acetate);

$^1$H-NMR (CD$_3$OD): δ1.94-2.02, 3.14, 5.20-5.32, 7.20-7.24, 7.55-7.62, 7.66-7.76, 7.96-8.02, 8.83-8.90.

Examples 5-15: 6-amino-9-[(2S)-2-butyl]-7-(7-fluoro-1H-indazol-4-yl)-2-{[2-fluoro-4-(methylsulfonyl)phenyl]amino}-7,9-dihydro-8H-purin-8-one

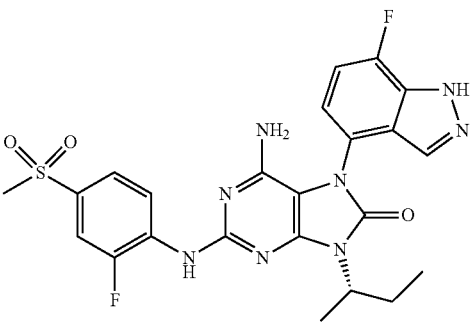 [SMILES: CC[C@H](C)n1c(=O)n(-c2ccc(F)c3[nH]ncc23)c2c(N)nc(Nc3ccc(S(C)(=O)=O)cc3F)nc21]

Purity (LC-MS/ELSD) Condition 1: 100% (Retention time: 0.86 minutes);

MASS (ESI, Pos.): 529 (M+H)$^+$;

$^1$H-NMR (CDCl$_3$): δ0.92-1.01, 1.64-1.69, 1.86-2.02, 2.19-2.37, 3.07, 4.34, 4.50-4.63, 7.08-7.15, 7.18-7.25, 7.28-7.34, 7.62-7.68, 7.70-7.79, 8.00-8.07, 8.79-8.86.

Examples 5-16: 6-amino-7-(4-chloro-3-hydroxyphenyl)-9-(3,3-difluorocyclopentyl)-2-{[2-fluoro-4-(1-piperazinylcarbonyl)phenyl]amino}-7,9-dihydro-8H-purin-8-one

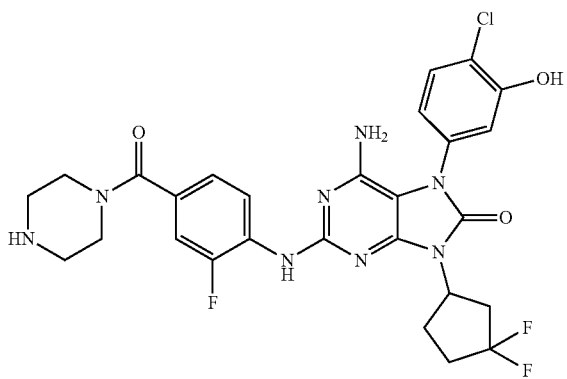 [SMILES: Nc1nc(Nc2ccc(C(=O)N3CCNCC3)cc2F)nc2c1n(-c1ccc(Cl)c(O)c1)c(=O)n2C1CCC(F)(F)C1]

TLC: Rf 0.27 (ethyl acetate:methanol=3:1);

$^1$H-NMR (CDCl$_3$): δ2.10-2.32, 2.42-2.73, 2.81-2.99, 3.08-3.25, 3.43-3.80, 4.49, 4.99-5.12, 6.96-7.00, 7.07-7.18, 7.19-7.40, 7.43-7.51, 8.42-8.50.

Examples 5-17: 6-amino-7-(1H-indol-5-yl)-9-isopropyl-2-[(2-methyl-1-oxo-2,3-dihydro-1H-isoindol-5-yl)amino]-7,9-dihydro-8H-purin-8-one trifluoroacetate

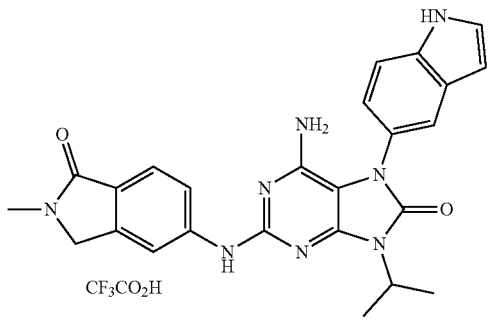 [SMILES: CC(C)n1c(=O)n(-c2ccc3[nH]ccc3c2)c2c(N)nc(Nc3ccc4c(c3)CN(C)C4=O)nc21 ; "CF3CO2H"]

Purity (LC-MS/ELSD) Condition 1: 100% (Retention time: 0.78 minutes);
MASS (ESI, Pos.): 469 (M+H)+;
$^1$H-NMR (DMSO-d$_6$): δ1.47-1.60, 3.02, 4.38, 4.60-4.70, 5.25-5.50, 6.51-6.55, 7.00-7.04, 7.43-7.50, 7.63-7.68, 7.72-7.79, 8.17, 9.36, 11.35.

Examples 5-18: 6-amino-2-[(1,3-dimethyl-1H-pyrazol-4-yl)amino]-7-(1H-indol-6-yl)-9-isopropyl-7,9-dihydro-8H-purin-8-one

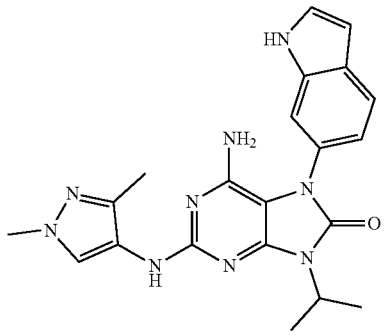 [SMILES: Cc1nn(C)cc1Nc1nc(N)c2c(n1)n(C(C)C)c(=O)n2-c1ccc2cc[nH]c2c1]

TLC: Rf 0.22 (ethyl acetate);
$^1$H-NMR (CDCl$_3$): δ1.60-1.68, 2.25, 3.84, 4.28, 4.71-4.82, 6.16, 6.58-6.61, 7.09-7.15, 7.29-7.32, 7.54, 7.71-7.75, 7.78, 8.41-8.55.

Examples 5-19: 4-{[6-amino-7-(1H-indol-5-yl)-9-isopropyl-8-oxo-8,9-dihydro-7H-purin-2-yl]amino}-3-fluoro-N,N-dimethylbenzamide

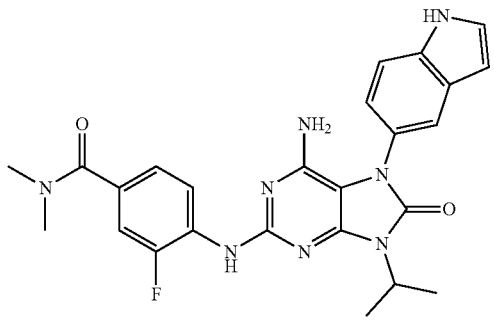 [SMILES: CC(C)n1c(=O)n(-c2ccc3[nH]ccc3c2)c2c(N)nc(Nc3ccc(C(=O)N(C)C)cc3F)nc21]

Purity (LC-MS/ELSD) Condition 1: 99.8% (Retention time: 1.03 minutes);
MASS (ESI, Pos.): 489 (M+H)+;
$^1$H-NMR (CDCl$_3$): δ1.58-1.66, 3.09, 4.71-4.86, 6.52-6.59, 7.02-7.08, 7.20-7.29, 7.38, 7.51-7.58, 7.67-7.73, 8.42-8.50, 9.05.

Examples 5-20: 6-amino-9-cyclopentyl-7-(3-hydroxyphenyl)-2-({4-[2-(1-pyrrolidinyl)ethyl]phenyl}amino)-7,9-dihydro-8H-purin-8-one

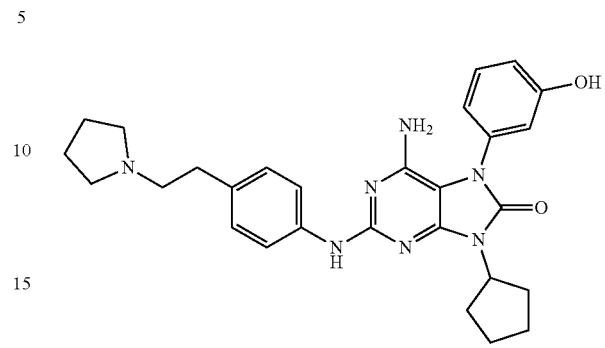

Purity (LC-MS/ELSD) Condition 1: 97% (Retention time: 0.64 minutes);
MASS (ESI, Pos.): 500 (M+H)+.

Examples 5-21: 4-{[6-amino-9-cyclopentyl-7-(3-hydroxyphenyl)-8-oxo-8,9-dihydro-7H-purin-2-yl]amino}-3-methoxy-N,N-dimethylbenzamide Purity (LC-MS/ELSD) Condition 1: 99.8% (Retention time: 0.83 minutes);
MASS (ESI, Pos.): 504 (M+H)+;
$^1$H-NMR (DMSO-d$_6$): δ1.61-1.69, 1.86-1.98, 2.15-2.30, 2.98, 3.91, 4.70-4.79, 5.64, 6.78-6.84, 6.95-7.00, 7.05, 7.30-7.35, 7.47, 8.46-8.49, 9.86.

Examples 5-22: 4-{[6-amino-7-(4-chloro-3-hydroxyphenyl)-9-isopropyl-8-oxo-8,9-dihydro-7H-purin-2-yl]amino}-N-[2-(dimethylamino)ethyl]-3-fluorobenzamide

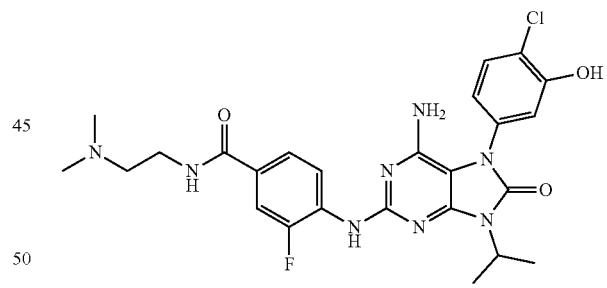

TLC: Rf 0.33 (ethyl acetate:methanol=1:4);
$^1$H-NMR (CD$_3$OD): δ1.58-1.67, 2.33, 2.56-2.63, 3.49-3.57, 4.68-4.80, 6.78-6.84, 6.94, 7.41-7.47, 7.60-7.71, 7.75-7.84, 8.60-8.68.

Examples 5-23: 6-amino-9-cyclopentyl-2-{[2-fluoro-4-(4-morpholinylcarbonyl) phenyl]amino}-7-(3-hydroxyphenyl)-7,9-dihydro-8H-purin-8-one Purity (LC-MS/ELSD) Condition 1: 99.4% (Retention time: 0.84 minutes);
MASS (ESI, Pos.): 534 (M+H)+;
$^1$H-NMR (CDCl$_3$): δ1.67-1.77, 1.96-2.09, 2.30-2.42, 3.59-3.78, 4.45, 4.82-4.95, 6.23, 6.85-6.94, 7.08, 7.19-7.24, 7.34-7.39, 8.54-8.61.

Examples 5-24: 4-{[6-amino-9-cyclopentyl-7-(3-hydroxyphenyl)-8-oxo-8,9-dihydro-7H-purin-2-yl]amino}benzamide Purity (LC-MS/ELSD) Condition 1: 99.7% (Retention time: 0.93 minutes);
MASS (ESI, Pos.): 446 (M+H)⁺;
¹H-NMR (DMSO-d₆): δ1.65-1.75, 1.90-2.10, 2.23-2.38, 4.72-4.85, 5.54, 6.80-6.95, 7.09, 7.31-7.38, 7.71-7.95, 9.27, 9.89.

Examples 5-25: 6-amino-9-cyclopentyl-7-(3-hydroxyphenyl)-2-{[4-(4-morpholinyl) phenyl]amino}-7,9-dihydro-8H-purin-8-one

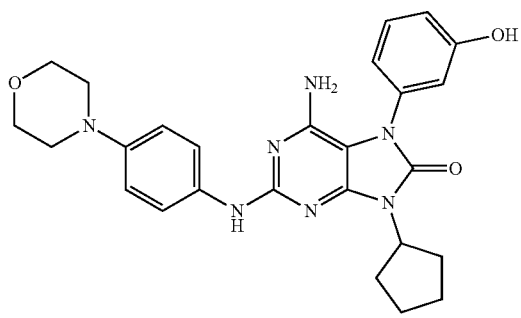 [SMILES: Nc1nc(Nc2ccc(N3CCOCC3)cc2)nc2c1n(-c1cccc(O)c1)c(=O)n2C1CCCC1]

Purity (LC-MS/ELSD) Condition 1: 99% (Retention time: 0.75 minutes);
MASS (ESI, Pos.): 488 (M+H)⁺.

Examples 5-26: 4-{[⁶-amino-9-cyclopentyl-7-(3-hydroxyphenyl)-8-oxo-8,9-dihydro-7H-purin-2-yl]amino}-3-fluoro-N-(2-hydroxyethyl)benzamide

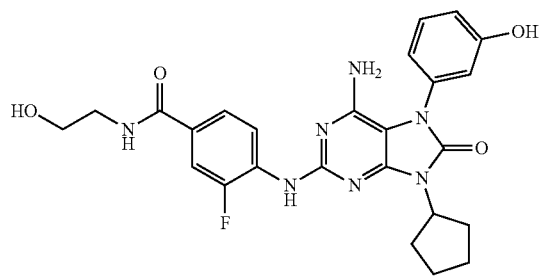 [SMILES: Nc1nc(Nc2ccc(C(=O)NCCO)cc2F)nc2c1n(-c1cccc(O)c1)c(=O)n2C1CCCC1]

Purity (LC-MS/ELSD) Condition 1: 99.8% (Retention time: 0.77 minutes);
MASS (ESI. Pos.): 508 (M+H)⁺;
¹H-NMR (DMSO-d₆): δ1.65-1.66, 1.83-1.96, 2.16-2.28, 3.24-3.36, 3.47-3.55, 4.69-4.78, 5.55, 6.78-6.87, 7.29-7.34, 7.64-7.72, 8.25-8.30, 8.35-8.41, 9.91.

Examples 5-27: 6-amino-2-({2-fluoro-4-[(4-hydroxy-1-pyridinyl)carbonyl] phenyl}amino)-7-(1H-indol-5-yl)-9-(tetrahydro-3-furanyl)-7,9-dihydro-8H-purin-8-one Purity (LC-MS/ELSD) Condition 1: 99.9% (Retention time: 0.67 minutes);
MASS (ESI, Pos.): 573 (M+H)⁺;
¹H-NMR (DMSO-d₆): δ1.32-1.42, 1.72-1.81, 2.18-2.27, 3.16-3.23, 3.72-3.85, 3.93-4.07, 4.77, 4.96-5.04, 5.28, 6.53, 7.12-7.15, 7.21-7.25, 7.48-7.55, 7.64, 8.11-8.18, 8.36, 11.39.

Examples 5-28: 5-{[6-amino-7-(1H-indol-5-yl)-9-isopropyl-8-oxo-8,9-dihydro-7H-purin-2-yl]amino}-N,N-dimethyl-2-pyridinecarboxamide

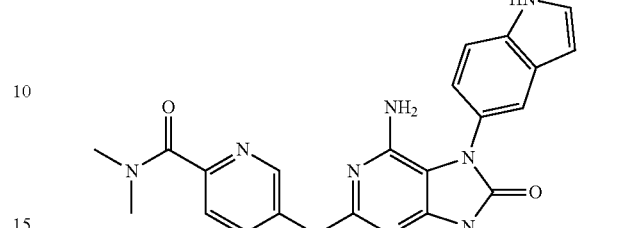

Purity (LC-MS/ELSD) Condition 2: 100% (Retention time: 0.72 minutes);
MASS (ESI, Pos.): 472 (M+H)⁺.

Examples 5-29: 6-amino-7-(1H-indol-5-yl)-9-isopropyl-2-[(2-methyl-4-oxo-4H-chromen-7-yl)amino]-7,9-dihydro-8H-purine-8-one

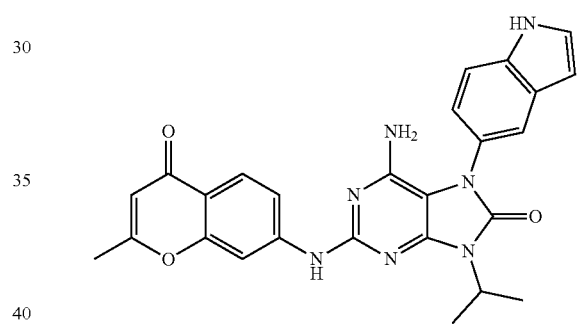

Purity (LC-MS/ELSD) Condition 2: 100% (Retention time: 0.89 minutes);
MASS (ESI, Pos.): 482 (M+H)⁺.

Examples 5-30: 6-amino-7-(1H-indol-5-yl)-9-isopropyl-2-[(1-oxo-1,3-dihydro-2-benzofuran-5-yl)amino]-7,9-dihydro-8H-purin-8-one

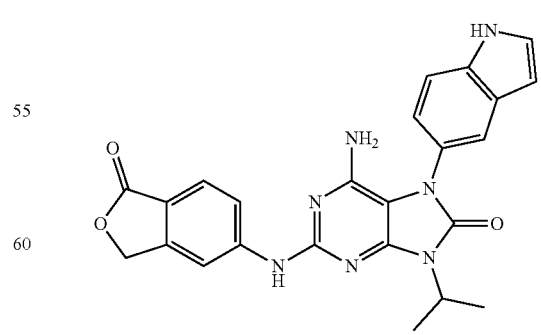

Purity (LC-MS/ELSD) Condition 2: 99% (Retention time: 0.87 minutes);
MASS (ESI, Pos.): 456 (M+H)⁺.

Examples 5-31: 7-{[6-amino-7-(1H-indol-5-yl)-9-isopropyl-8-oxo-8,9-dihydro-7H-purin-2-yl]amino}-4-methyl-2H-1,4-benzoxazin-3(4H)-one

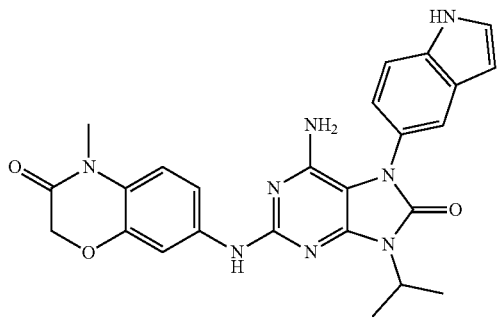 [SMILES: CC(C)n1c(=O)n(-c2ccc3[nH]ccc3c2)c2c(N)nc(Nc3ccc4c(c3)OCC(=O)N4C)nc21]

Purity (LC-MS/ELSD) Condition 1: 100% (Retention time: 0.81 minutes);
MASS (ESI, Pos.): 485 (M+H)$^+$.

Examples 5-32: 4-{[6-Amino-7-(1H-indol-5-yl)-8-oxo-9-(tetrahydro-3-furanyl)-8,9-dihydro-7H-purin-2-yl]amino}-3-fluorobenzenesulfonamide

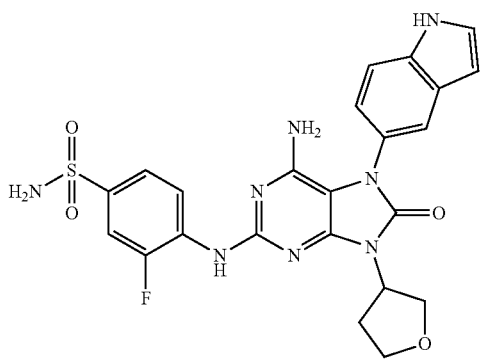 [SMILES: Nc1nc(Nc2ccc(S(N)(=O)=O)cc2F)nc2c1n(-c1ccc3[nH]ccc3c1)c(=O)n2C1CCOC1]

Purity (LC-MS/ELSD) Condition 1: 99% (Retention time: 0.72 minutes):
MASS (ESI, Pos.): 525 (M+H)$^+$;
$^1$H-NMR (DMSO-d$_6$): δ2.20-2.29, 2.45-2.55, 3.82-3.89, 3.99-4.03, 4.08-4.12, 4.99-5.07, 5.34, 6.53, 7.12-7.15, 7.32, 7.48-7.59, 7.65, 8.42-8.47, 8.50, 11.40.

PHARMACOLOGICAL EXPERIMENTAL EXAMPLES

Pharmacological Experimental Example 1: Measurement of Brk Inhibitory Activity Measurement of an inhibitory activity on Brk enzyme was performed by using LanthaScreen (registered trademark) system (Invitrogen) in accordance with the attached manual. Reagents used are described below.
Reaction Buffer: A solution containing 50 mmol/L HEPES (pH 7.5), 0.01% Brij 35, 10 mmol/L MgCl$_2$ and 1 mmol/L EGTA was prepared by using purified water.
A solution of a test substance (the compound of the present invention): A solution of each concentration of a test compound in DMSO was diluted 20-fold with Reaction Buffer, and a solution containing a test compound at a concentration 5 times a final concentration was prepared.
An enzyme solution: A solution containing 480 ng/mL of Brk enzyme was prepared by using Reaction Buffer.
A substrate solution: A solution containing 57 μmol/L of ATP and 500 nmol/L of Fluorescein-Poly GT (Invitrogen) was prepared by using Reaction Buffer.
A detection solution: A solution containing 20 mmol/L of EDTA and 4 nmol/L of PY20 (Invitrogen) was prepared by using Dilution B (Invitrogen).
To a 96-well plate (Nunc), a solution of 10 mmol/L of a test compound in DMSO was dispensed, and further, a dilution series at a common ratio of three was prepared by using DMSO. To each of wells of the 96-well plate for the measurement, 5 μL of Reaction Buffer containing DMSO was added for a blank group and a vehicle group and 5 μL of a test substance solution was added for a test substance group. Next, 10 μL per well of Reaction Buffer was added for the blank group, and 10 μL per well of the enzyme solution was added for the vehicle group and the test compound group, and thereafter, the mixture was stirred at room temperature for 10 minutes. After completion of stirring, 10 μL of the substrate solution was added to each of wells, and the mixture was stirred at room temperature under a shading condition for 1 hour. After completion of the reaction, 25 μL of the detection solution was added to each well, and the mixture was left to stand at room temperature under a shading condition for 30 minutes. After being left standing, fluorescence intensities at 520 nm and 495 nm were measured by using Analyst GT (Molecular Devices, LLC) when being irradiated with an excitation light at 340 nm. The phosphorylation of the artificial substrate was quantified by Time-Resolved Fluorescence Resonance Energy Transfer (TR-FRET). With regard to each well, the TR-FRET ratio was calculated by divining the fluorescence signal at 520 run by the fluorescence signal at 495 nm, and the inhibition rate (%) in the test compound group was calculated according to the following Numerical Formula 1.

Inhibition rate (%)=
{1−(TR-FRET ratio of test compound group−$A$)/($B$−$A$)}×100   [Numerical Formula 1]

A: Mean value of TR-FRET ratio of blank group
B: Mean value of TR-FRET ratio of vehicle group
The value (IC$_{50}$ value) of 50% inhibition rate of the test compound was calculated from the inhibition curve based on the inhibition rate at each concentration of the test compound.
As a result, it was found that each IC$_{50}$ value of the compounds of the present invention was equal to or lower than 0.1 μmol/L, and the compound of the present invention has a potent Brk inhibitory activity. For example, IC$_{50}$ values of several compounds of the present invention were as shown in the following Table 1.

TABLE 1

| Example No. | Brk inhibitory activity (IC$_{50}$: μmol/L) |
|---|---|
| 1 | 0.007 |
| 2-1 | 0.009 |
| 2-2 | 0.010 |
| 3 | 0.005 |
| 4 | 0.011 |
| 5-1 | 0.002 |
| 5-2 | 0.005 |
| 5-3 | 0.006 |
| 5-4 | 0.006 |
| 5-5 | 0.007 |

TABLE 1-continued

| Example No. | Brk inhibitory activity (IC$_{50}$: μmol/L) |
|---|---|
| 5-8 | 0.009 |
| 5-10 | 0.021 |
| 5-11 | 0.022 |
| 5-16 | 0.002 |
| 5-17 | 0.003 |
| 5-18 | 0.003 |
| 5-19 | 0.003 |
| 5-21 | 0.005 |
| 5-22 | 0.007 |
| 5-27 | 0.014 |
| 5-32 | 0.054 |

Pharmacological Experimental Example 2: Tests of Enzyme Inhibitory Activities on Kinases Other than Brk (Experiment on Selectivity)

The compound of the present invention was dissolved in DMSO to prepare a solution with a concentration of 100 times the test concentration of 1 μmol/L. The solution was further diluted 25-fold with Assay Buffer (20 mmol/L HEPES, 0.01% Triton X-100, 2 mmol/L DTT, pH 7.5) to give a test substance solution. With regard to a positive control substance, a solution of the positive control substance was prepared in a similar manner.

Five microliters of a test substance solution with a concentration of four times prepared by using Assay Buffer, 5 μL of a solution of a substrate/ATP/a metal (Mg) with a concentration of four times and 10 μL of a solution of kinase with a concentration of two times were mixed in a well of a 384-well plate made of polypropylene, and the mixture was subjected to a reaction at room temperature for 1 hour. To the mixture, 60 μL of Termination Buffer (QuickScout Screening Assist MSA; Cama Biosciences, Inc.) was added to stop the reaction. The substrate peptide and the phosphorylated peptide in the reaction solution were separated, and were quantified. The kinase reaction was evaluated by a product ratio (P/(P+S)) calculated from a peak height (S) of the substrate peptide and a peak height (P) of the phosphorylated peptide. As other kinases, kinase selectivity experiments were performed using, for example, the p38α and Syk kinases. Table 2 below shows the substrate, substrate concentration, ATP concentration, and positive control substance used for each kinase enzyme inhibitory activity test.

TABLE 2

| kinase | substrate name | substrate (μmol/L) | ATP (mmol/L) | Positive control |
|---|---|---|---|---|
| p38α | Modified Erktide | 1 | 1 | SB202190 |
| Syk | Blk/Lyntide | 1 | 1 | Staurosporine |

The average signal of control wells containing all the reaction concretes was 0% inhibition, and the average signal of background wells (no enzyme added) was 100% inhibition, and inhibition rates was calculated from the average signal of each experimental substance test well. For example, the inhibition rates of the compounds of the present invention on the kinases in Example 3 and Example 4 at a concentration of 1 μmol/L were as shown in the following Table 3.

TABLE 2

| | inhibition rates (%) | |
|---|---|---|
| kinase | Example 3 | Example 4 |
| p38α | 24 | 0 |
| Syk | 0 | 0 |

The compounds of the present invention were found to have strong inhibitory activity against Brk and to have excellent kinase selectivity. For example, as shown in Table 3 above, Example 3 and Example 4 of the compound of the present invention have 24% or less inhibition (compound concentration of 1 μmol/L) against p38α and Syk kinases. On the other hand, the IC$_{50}$ of inhibitory activity against Brk was 0.005 μmol/L and 0.011 μmol/L, respectively (from Pharmacological Experiment 1).

Preparation Examples

The following ingredients can be mixed in a conventional manner and compressed to give 10,000 tablets each containing 10 mg of the active ingredient.
2-[(4-acetyl-2-fluorophenyl)amino]-6-amino-7-(1H-indazol-4-yl)-9-isopropyl-7,9-dihydro-8H-purin-8-one . . . 100 g
Carboxymethyl cellulose calcium (a disintegrating agent) . . . 20 g
Magnesium stearate (a lubricant) . . . 10 g
Microcrystalline cellulose . . . 870 g

INDUSTRIAL APPLICABILITY

The compound of the present invention has a Brk inhibitory activity, and is effective for the treatment of diseases in which Brk involves, for example, cancer and the like.

The invention claimed is:
1. A compound represented by formula (I):

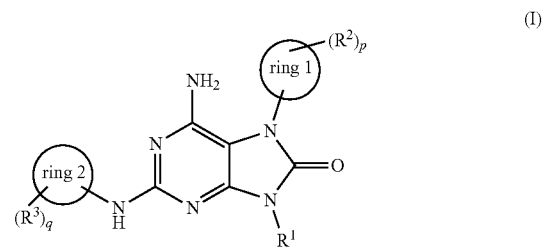

wherein:
ring1 and ring2 each independently represent a C5-10 carbocycle or a 5- to 10-membered heterocycle;
R$^1$-represents a C1-4 alkyl, a C2-4 alkenyl, a C2-4 alkynyl, a C3-6 cycloalkyl, or a 3- to 6-membered heterocycloalkyl, said C1-4 alkyl, C2-4 alkenyl, C2-4 alkynyl, C3-6 cycloalkyl, or 3- to 6-membered heterocycloalkyl may be substituted with a 1-5 halogen or a hydroxyl group;
R$^2$ represents a halogen, a C1-4 alkyl, OR$^4$, NR$^5$R$^6$, or an oxo, said C1-4 alkyl may be substituted with a 1-5 halogen;
R$^4$ represents a hydrogen atom, a C1-4 alkyl, or a benzene ring, said C1-4 alkyl or benzene ring may be substituted with a 1-5 halogen;

R[5] and R[6] each independently represent a hydrogen atom or a C1-4 alkyl;

R[3] represents a halogen, a C1-4 alkyl, OR[7], NR[8]R[9], SO₂R[10], COR[11], a benzene ring, a 4-to 6-membered heterocycle, or an oxo, said C1-4 alkyl may be substituted with 1-5 substituents which are selected from the group consisting of a halogen, a hydroxyl group, a 4- to 6-membered heterocycle, and CONR[12]R[13];

R[7] represents a hydrogen atom or a C1-4 alkyl, said C1-4 alkyl may be substituted with a 1-5 halogen or NR[14]R[15];

R[8] and R[9] each independently represent a hydrogen atom, a C1-4 alkyl, or acetyl;

R[10] represents a C1-4 alkyl or NR[16]R[17];

R[11] represents a hydroxyl group, a C1-4 alkyl, NR[18]R[19], or a 4- to 6-membered heterocycle, said 4- to 6-membered heterocycle may be substituted with 1-5 substituents which are selected from the group consisting of a halogen, a hydroxyl group, and a C1-4 alkyl;

R[12], R[13], R[14], R[15], R[16] and R[17] each independently represent a hydrogen atom or a C1-4 alkyl;

R[18] and R[19] each independently represent a hydrogen atom, a C1-4 alkyl, or a 4- to 6-membered heterocycle, said C1-4 alkyl may be substituted with a 1-5 hydroxyl group, a C1-3 alkoxy, or NR[20]R[21];

R[20] and R[21] each independently represent a hydrogen atom or a C1-4 alkyl;

p represents an integer of 0 to 7;

q represents an integer of 0 to 7;

provided that when p and q each represent an integer of 2 or more, R[2] and R[3] each independently may be the same or different;

a salt thereof or a solvate thereof.

2. The compound according to claim 1, a salt thereof or a solvate thereof, wherein R[1] is isopropyl, tert-butyl, isobutyl, a C3-6 cycloalkyl, or a 3- to 6-membered heterocycloalkyl that may be substituted with a 1-5 halogen or a hydroxyl group.

3. The compound according to claim 1, a salt thereof or a solvate thereof, wherein ring1 is a 9- to 10-membered nitrogen-containing bicyclic aromatic heterocycle.

4. The compound according to claim 1, a salt thereof or a solvate thereof, wherein ring2 is a benzene ring.

5. The compound according to claim 1, a salt thereof or a solvate thereof, wherein q is an integer of 1 or more, R[3] is at least one a halogen, a C1-3 alkoky, SO₂R[10], or COR[11].

6. The compound according to claim 1, which is represented by formula (I-1):

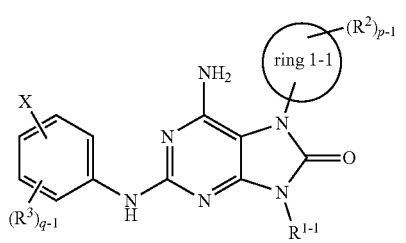

(I-1)

wherein, ring1-1 represents indol ring or indazole ring, R[1-1] represents isopropyl, tert-butyl, cyclobutyl, cyclopentyl, difluorocyclopentyl, oxetanyl, or tetrahydrofuranyl, X represents a halogen, p-1 represents an integer of 0 to 6, q-1 represents an integer of 0 to 4;

a salt thereof or a solvate thereof.

7. The compound according to claim 1, which is represented by formula (I-1'):

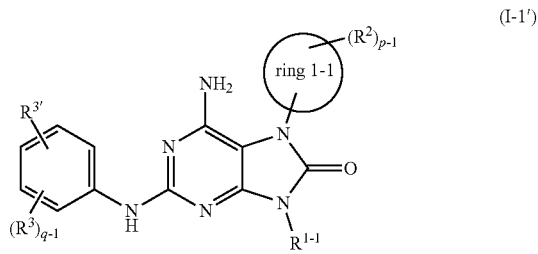

(I-1')

wherein, R[3'] represents SO₂R[10] or COR[11], R[1-1] represents isopropyl, tert-butyl, cyclobutyl, cyclopentyl, difluorocyclopentyl, oxetanyl, or tetrahydrofuranyl, p-1 represents an integer of 0 to 6, q-1 represents an integer of 0 to 4;

a salt thereof or a solvate thereof.

8. A compound according to the claim 1, which is:

(1) 6-amino-7-(7-fluoro-1H-indazole-4-yl)-2-{[2-fluoro-4-(methylsulfonyl)phenyl]amino}-9-isopropyl-7,9-dihydro-8H-purine-8-one;

(2) 6-amino-7-(7-chloro-1H-indazol-4-yl)-2-{[2-fluoro-4-(methylsulfonyl)phenyl] amino}-9-isopropyl-7,9-dihydro-8H-purine-8-one;

(3) 6-amino-7-(6,7-difluolo-1H-indazol-4-yl)-2-{[2-fluoro-4-(methylsulfonyl)phenyl] amino}-9-isopropyl-7,9-dihydro-8H-purine-8-one;

(4) 6-amino-7-(7-fluolo-1H-indazol-4-yl)-2-{[2-fluoro-4-(methylsulfonyl)phenyl] amino}-9-(2-methyl-2-propanyl)-7,9-dihydro-8H-purine-8-one;

(5) 2-[(4-acetyl-2-fluorophenyl)amino]-6-amino-7-(1H-indazol-4-yl)-9-isopropyl-7,9-dihydro-8H-purine-8-one;

(6) 6-amino-9-cyclopentyl-2-{[2-fluoro-4-(methylsulfonyl)phenyl]amino}-7-(1H-indazol-4-yl)-7,9-dihydro-8H-purine-8-one;

(7) 6-amino-9-cyclobutyl-2-{[2-fluoro-4-(methylsulfonyl)phenyl]amino}-7-(1H-indazol-4-yl)-7,9-dihydro-8H-purine-8-one;

(8) 6-amino-2-{[2-fluoro-4-(methyl sulfonyl)phenyl] amino}-7-(1H-indazol-4-yl)-9-(2-methyl-2-propanyl)-7,9-dihydro-8H-purine-8-one;

(9) 6-amino-2-{[2-fluoro-4-(methyl sulfonyl)phenyl] amino}-9-isopropyl-7-(7-methyl-1H-indazol-4-yl)-7,9-dihydro-8H-purine-8-one;

(10) 6-amino-9-(3,3-difluorocyclopentyl)-2-{[2-fluoro-(methylsulfonyl)phenyl] amino}-7-(1H-indazol-4-yl)-7,9-dihydro-8H-purine-8-one;

(11) 6-amino-7-(7-chloro-1H-indazol-4-yl)-9-isopropyl-2-{[2-methoxy-4-(methylsulfonyl)phenyl] amino}-7,9-dihydro-8H-purine-8-one;

(12) 6-amino-7-(7-fluoro-1H-indazol-4-yl)-2-{[2-methoxy-4-(methylsulfonyl)phenyl] amino}-9-(2-methyl-2-propanyl)-7,9-dihydro-8H-purine-8-one;

(13) 6-amino-2-{(2-fluoro-4-(methylsulfonyl)phenyl] amino}-7-(1H-indazol-6-yl)-9-(tetrahydro-3-furanyl)-7,9-dihydro-8H-purine-8-one;

(14) 6-amino-9-cyclopentyl-2-{(2-fluoro-4-(methylsulfonyl)phenyl]amino}-7-(3-hydroxyphenyl)-7,9-dihydro-8H-purine-8-one;

(15) 6-amino-2-{[2,3-difluoro-4-(methylsulfonyl)phenyl] amino}-7-(7-fluoro-1H-indazol-4-yl)-9-isopropyl-7,9-dihydro-8H-purine-8-one;
(16) 6-amino-2-{[2,5-difluoro-4-(methylsulfonyl)phenyl] amino}-7-(7-fluoro-1H-indazol-4-yl)-9-isopropyl-7,9-dihydro-8H-purine-8-one;
(17) 6-amino-7-(3-amino-4-fluorophenyl)-2-{[2-fluoro-4-(methyl sulfonyl)phenyl] amino}-9-isopropyl-7,9-dihydro-8H-purine-8-one;
(18) 6-amino-7-(1-benzofuran-5-yl)-2-{[2-fluoro-4-(methyl sulfonyl)phenyl]amino}-9-isopropyl-7,9-dihydro-8H-purine-8-one;
(19) 6-amino-2-{[2-fluoro-4-(methylsulfonyl)phenyl] amino}-7-(1H-indazol-4-yl)-9-(1,1,1-trifluoro-2-propanyl)-7,9-dihydro-8H-purine-8-one;
(20) 6-amino-9-[(2S)-2-butanyl]-7-(7-fluoro-1H-indazol-4-yl)-2-{[2-fluoro-4-(methylsulfonyl)phenyl]amino}-7,9-dihydro-8H-purine-8-one;
(21) 6-amino-7-(4-chloro-3-hydroxyphenyl)-9-(3,3-difluorocyclopentyl)-2-{[2-fluoro-4-(1-piperazinylcarbonyl)phenyl]amino}-7,9-dihydro-8H-purine-8-one;
(22) 6-amino-7-(1H-indol-5-yl)-9 isopropyl-2-[(2-methyl-1-oxo-2,3-dihydro-1H-isoindole-5-yl)amino]-7,9-dihydro-8H-purine-8-one;
(23) 6-amino-2-[(1,3-dimethyl-1H-pyrazole-4-yl)amino]-7-(1H-indole-6-yl)-9-isopropyl-7,9-dihydro-8H-purine-8-one;
(24) 4-{[(6-amino-7-(1H-indole-5-yl)-9-isopropyl-8-oxo-8,9-dihydro-7H-purine-2-yl]amino}-3-fluoro-N,N-dimethylbenzamide;
(25) 6-amino-9-cyclopentyl-7-(3-hydroxyphenyl)-2-({4-[2-(1-pyrrolidynyl)ethyl] phenyl} amino)-7,9-dihydro-8H-purine-8-one;
(26) 4-{[(6-amino-9-cyclopentyl-7-(3-hydroxyphenyl)-8-oxo-8,9-dihydro-7H-purine-2-yl]amino}-3-methoxy-N,N-dimethylbenzamide;
(27) 4-{[(6-amino-7-(4-chloro-3-hydroxyphenyl)-9-isopropyl-8-oxo-8,9-dihydro-7H-purine-2-yl] amino}-N-[2-(dimethylamino) ethyl]-3-fluorobenzamide;
(28) 6-amino-9-cyclopentyl-2-{[2-fluoro-4-(4-morpholinylcarbonyl)phenyl]amino}-7-(3-hydroxyphenyl)-7,9-dihydro-8H-purine-8-one;
(29) 4-{[6-amino-9-cyclopentyl-7-(3-hydroxyphenyl)-8-oxo-8,9-dihydro-7H-purine-2-yl]amino}benzamide;
(30) 6-amino-9-cyclopentyl-7-(3-hydroxyphenyl)-2-{[4-(4-morpholinyl)phenyl]amino}-7,9-dihydro-8H-purine-8-one;
(31) 4-{[6-amino-9-cyclopentyl-7-(3-hydroxyphenyl)-8-oxo-8,9-dihydro-7H-purine-2-yl] amino}-3-fluoro-N-(2-hydroxyethyl)benzamide;
(32) 6-amino-2-({2-fluoro-4-[(4-hydroxy-1-piperidinyl) carbonyl]phenyl}amino)-7-(1H-indole-5-yl)-9-(tetrahydro-3-furanyl)-7,9-dihydro-8H-purine-8-one;
(33) 5-{[6-amino-7-(1H-indole-5-yl)-9-isopropyl-8-oxo-8,9-dihydro-7H-purine-2-yl] amino}-N,N-dimethyl-2-pyridinecarboxamide;
(34) 6-amino-7-(1H-indole-5-yl)-9-isopropyl-2-[(2-methyl-4-oxo-4H-chromene-7-yl) amino]-7,9-dihydro-8H-purine-8-one;
(35) 6-amino-7-(1H-indole-5-yl)-9-isopropyl-2-[(1-oxo-1,3-dihydro-2-benzofuran-5-yl) amino]-7,9-dihydro-8H-purine-8-one;
(36) 7-{[6-amino-7-(1H-indole-5-yl)-9-isopropyl-8-oxo-8,9-dihydro-7H-purine-2-yl] amino}-4-methyl-2H-1,4-benzoxazine-3(4H)-one, or
(37) 4-{[6-amino-7-(1H-indole-5-yl)-8-oxo-9-(tetrahydro-3-furanyl)-8,9-dihydro-7H-purine-2-yl]amino}-3-fluorobenzenesulfonamide;
a salt thereof or a solvate thereof.

9. A pharmaceutical composition comprising the compound represented by formula (I) according to claim 1, a salt thereof or a solvate thereof as an active ingredient and a pharmaceutically acceptable carrier.

10. A medicament comprising the compound represented by formula (I) according to claim 1, a salt thereof or a solvate thereof in combination with at least one kind of additional agent selected from an alkylating agent, an antimetabolite, an anticancer antibiotic, a plant-derived preparation, a hormone preparation, a platinum compound, a immunomodulator, a topoisomerase inhibitor, a biological response modifier, a kinase inhibitor, a histone deacetylase (HDAC) inhibitor, a proteasome inhibitor, an anti-CD20 antibody, an anti-HER2 antibody, an anti-EGFR antibody, and an anti-VEGF antibody.

11. A method for treating cancer comprising administering an effective amount of the compound represented by formula (I) according to the claim 1, a salt thereof or a solvate thereof to a patient in need of the treatment of cancer, wherein the cancer is breast cancer, ovarian cancer, colon cancer, pancreatic cancer, bladder cancer, esophageal cancer, gastric cancer, non-small cell lung cancer, prostate cancer, oral squamous cell cancer, head and neck squamous cell cancer, melanoma, B cell lymphoma, and T cell lymphoma.

12. A method for treating cancer comprising administering an effective amount of the pharmaceutical composition of claim 9 to a patient in need of the treatment of cancer, wherein the cancer is breast cancer, ovarian cancer, colon cancer, pancreatic cancer, bladder cancer, esophageal cancer, gastric cancer, non-small cell lung cancer, prostate cancer, oral squamous cell cancer, head and neck squamous cell cancer, melanoma, B cell lymphoma, and T cell lymphoma.

* * * * *